United States Patent
Dickson et al.

(10) Patent No.: US 12,023,366 B2
(45) Date of Patent: *Jul. 2, 2024

(54) EFFICIENT SYSTEMIC TREATMENT OF DYSTROPHIC MUSCLE PATHOLOGIES

(71) Applicants: GENETHON, Evry (FR); ROYAL HOLLOWAY AND BEDFORD NEW COLLEGE, Egham (GB); ASSOCIATION INSTITUT DE MYOLOGIE, Paris (FR); INSTITUT NATIONAL DE LA SANTE ET DE LA RECHERCHE MEDICALE, Paris (FR); CENTRE NATIONAL DE LA RECHERCHE SCIENTIFIQUE, Paris (FR); SORBONNE UNIVERSITE, Paris (FR); CENTRE HOSPITALIER UNIVERSITAIRE DE NANTES, Nantes (FR); NANTES UNIVERSITE, Nantes (FR)

(72) Inventors: George Dickson, London (GB); Thomas Voit, Boullay les Troux (FR); Philippe Moullier, Nantes (FR); Caroline Le Guiner, Granchamp des Fontaines (FR)

(73) Assignees: GENETHON, Evry (FR); ROYAL HOLLOWAY AND BEDFORD NEW COLLEGE, Surrey (GB); ASSOCIATION INSTITUT DE MYOLOGIE, Paris (FR); INSTITUT NATIONAL DE LA SANTE ET DE LA RECHERCHE MEDICALE, Paris (FR); CENTRE NATIONAL DE LA RECHERCHE SCIENTIFIQUE, Paris (FR); SORBONNE UNIVERSITE, Paris (FR); CENTRE HOSPITALIER UNIVERSITAIRE DE NANTES, Nantes (FR); NANTES UNIVERSITE, Nantes (FR)

( * ) Notice: Subject to any disclaimer, the term of this patent is extended or adjusted under 35 U.S.C. 154(b) by 470 days.

This patent is subject to a terminal disclaimer.

(21) Appl. No.: 17/000,867

(22) Filed: Aug. 24, 2020

(65) Prior Publication Data
US 2020/0405810 A1 Dec. 31, 2020

Related U.S. Application Data

(63) Continuation of application No. 16/185,248, filed on Nov. 9, 2018, now Pat. No. 10,786,546, which is a continuation of application No. 15/321,416, filed as application No. PCT/EP2015/058964 on Apr. 24, 2015, now Pat. No. 10,166,272.

(30) Foreign Application Priority Data

Jun. 27, 2014 (EP) .................... 14174848

(51) Int. Cl.
A61K 38/17 (2006.01)
A61K 48/00 (2006.01)
C12N 7/00 (2006.01)
C12N 15/86 (2006.01)

(52) U.S. Cl.
CPC ........ *A61K 38/1719* (2013.01); *A61K 48/005* (2013.01); *A61K 48/0058* (2013.01); *A61K 48/0075* (2013.01); *C12N 7/00* (2013.01); *C12N 15/86* (2013.01); *C12N 2750/14132* (2013.01); *C12N 2750/14143* (2013.01); *C12N 2750/14171* (2013.01); *C12N 2840/007* (2013.01)

(58) Field of Classification Search
None
See application file for complete search history.

(56) References Cited

U.S. PATENT DOCUMENTS 10,166,272 B2 * 1/2019 Dickson ............... A61K 48/005
10,786,546 B2 * 9/2020 Dickson ............... A61K 48/005

OTHER PUBLICATIONS

Arruda et al., "Peripheral transvenular delivery of adeno-associated viral vectors to skeletal muscle as a novel therapy for hemophilia B," *Blood* 115(23):4678-4688, Jun. 2010.

Athanasopoulos et al., "Recombinant adeno-associated viral (rAAV) vectors as therapeutic tools for Duchenne muscular dystrophy (DMD)," Abstract, *Gene Therapy* 11:S109-S121, 2004.

Barthélémy et al., "Longitudinal ambulatory measurements of gait abnormality in dystrophin-deficient dogs," *BMC Musculoskeletal Disorders* 12(75), Apr. 2011, 12 pages.

Bostick et al., "AAV micro-dystrophin gene therapy alleviates stress-induced cardiac death but no myocardial fibrosis in >21-m-old mdx mice, and end-stage model of Duchenne muscular dystrophy cardiomyopathy," *Journal of Molecular and Cellular Cardiology* 53:217-222, 2012.

Bowles et al., "Phase 1 Gene Therapy for Duchenne Muscular Dystrophy Using a Translational Optimized AAV Vector," *Molecular Therapy* 20(2):443-455, Feb. 2012.

Bushby et al., "Clinical outcome measures for trials in Duchenne muscular dystrophy: report from International Working Group meetings," *Clin. Investig. (Lond.)* 1(9):1217-1235, Sep. 2011.

Colgan et al., "511. Microdystrophin and Follistatin Combinatorial Gene Delivery to Treat a Severe Mouse Model of Duchenne Muscular Dystrophy," Abstract from ASGCT 17th Annual Meeting, Washington D.C., May 20-24, 2014, *Molecular Therapy* 22(S1):S197, May 2014.

(Continued)

Primary Examiner — Robert M Kelly
(74) Attorney, Agent, or Firm — Seed IP Law Group LLP

(57) ABSTRACT

A composition comprising a gene therapy product for use in the treatment of a dystrophic disease in a subject, advantageously in humans, wherein:
the gene therapy product comprises a nucleic acid sequence encoding a functional microdystrophin;
the composition is systemically administered.

9 Claims, 7 Drawing Sheets

Specification includes a Sequence Listing.

(56) References Cited

OTHER PUBLICATIONS

Dickson, "Optimised AAV Micro-Dystrophin Gene Therapy for Duchenne Muscular Dystrophy," PowerPoint Presentation, ASGCT 17th Annual Meeting, Washington D.C., May 20-24, 2014, 30 pages.
Dickson, "Optimised AAV-microdystrophin gene therapy in the GRMD dog model of Duchenne muscular dystrophy: intravenous delivery, long-term expression, functional improvement and absence of adverse cellular immune reactions," Abstract No. 350530, ASGCT 17th Annual Meeting, Washington D.C., May 20-24, 2014, Published Apr. 26, 2014, 2 pages.
Fan et al., "Safety and Feasibility of High-pressure Transvenous Limb Perfusion With 0.9% Saline in Human Muscular Dystrophy," *Molecular Therapy* 20(2):456-461, Feb. 2012.
Foster et al., "Codon and mRNA Sequence Optimization of Microdystrophin Transgenes Improves Expression and Physiological Outcome in Dystrophic mdx Mice Following AAV2/8 Gene Transfer," *Molecular Therapy* 16(11):1825-1832, Nov. 2008.
Gregorevic et al., "Systemic Microdystrophin Gene Delivery Improves Skeletal Muscle Structure and Function in Old Dystrophic mdx Mice," *Molecular Therapy* 16(4):657-664, Apr. 2008.
Jarmin et al., "New developments in the use of gene therapy to treat Duchenne muscular dystrophy," Abstract, *Expert Opin. Biol. Ther.* 14(2):209-230, Feb. 2014, retrieved from https://www.ncbi.nlm.gov/pubmed/2408293 on Dec. 14, 2016, 1 page.
Koo et al., "Genetic Therapy for Duchenne Muscular Dystrophy: Principles and Progress," in *Muscular Dystrophy*, Hegde (ed.), InTech, May 2012, 21 pages.
Koo et al., "Long-term functional adeno-associated virus-microdystrophin expression in the dystrophic CXMDj dog," *The Journal of Gene Medicine* 13:497-506, 2011.
Koppanati et al., "Improvement of the mdx mouse dystrophic phenotype by systemic in utero AAV8 delivery of a minidystrophin gene," *Gene Therapy* 17:1355-1362, 2010.
Kornegay et al., "Canine Models of Duchenne Muscular Dystrophy and Their Use in Therapeutic Strategies," Abstract, *Mamm. Genome.* 23:85-108, Feb. 2012, 1 page.
Le Guiner et al., "Long-term microdystrophin gene therapy is effective in a canine model of Duchenne muscular dystrophy," *Nature Communications* 8:16105, 15 pages, 2017.
McGreevy et al., "Animal models of Duchenne muscular dystrophy: from basic mechanisms to gene therapy," *Disease Models & Mechanisms* 8:195-213, 2015.
Mendell et al., "Dystrophin Immunity in Duchenne's Muscular Dystrophy," *New England Journal of Medicine* 363:1429-1437, Oct. 2010.
Moser, "Duchenne muscular dystrophy: pathogenetic aspects and genetic prevention," Abstract, *Human Genetics* 66(1):17-40, 1984, retrieved from https://www.ncbi.nlm.nih.gov/pubmed/?term=moser+1984+duchenne on Dec. 14, 2016, 1 page.
Muntoni et al., "Dystrophin and mutations: one gene, several proteins, multiple phenotypes," Abstract, *Lancet Neurol.* 2(12):731-740, Dec. 2003, retrieved from https://www.ncbi.nlm.nih.gov/pubmed/14636778 on Dec. 14, 2016, 1 page.
Odom et al., "Gene Therapy of mdx Mice With Large Truncated Dystrophins Generated by Recombination Using rAAV6" *Molecular Therapy* 19(1):36-45, Jan. 2011.
Ohshima et al., "Transduction Efficiency and Immune Response Associated With the Administration of AAV8 Vector Into Dog Skeletal Muscle," *Molecular Therapy* 17(1):73-80, Jan. 2009.
Peters et al., "Development and application of multiple internal reference (housekeeper) gene assays for accurate normalisation of canine gene expression studies," Abstract, *Vet. Immunol. Immunopathol.* 117(1-2):55-66, May 2007, retrieved from https://www.ncbi.nlm.nih.gov/pubmed/17346803 on Dec. 14, 2016, 1 page.
Rodino-Klapac et al., "Update on the treatment of Duchenne muscular dystrophy," Abstract, *Curr. Neurol. Neurosci. Rep.* 13(3):332, Mar. 2013, retrieved from https://www.ncbi.nih.gov/pubmed/23328943 on Dec. 14, 2016, 1 page.
Rouger et al., "Systemic Delivery of Allogenic Muscle Stem Cells Induces Long-Term Muscle Repair and Clinical Efficacy in Duchenne Muscular Dystrophy Dogs," *The American Journal of Pathology* 179(5):2501-2518, Nov. 2011.
Schinkel et al., "Long-Term Preservation of Cardiac Structure and Function After Adeno-Associated Virus Serotype 9-Mediated Microdystrophin Gene Transfer in mdx Mice," *Human Gene Therapy* 23:566-575, Jun. 2012.
Shin et al., "19. Efficient Systemic Delivery of RAAV8 into Dystrophic Animals by Subcutaneous Injections," Abstract from the 13th Annual Meeting 2007 Japan Society of Gene Therapy, Nagoya, Japan, Jun. 28-30, 2007, *Journal of Gene Medicine* 10:449, 2008.
Shin et al., "Improvement of cardiac fibrosis in dystrophic mice by rAAV9-mediated microdystrophin transduction," *Gene Therapy* 18:910-919, 2011.
Thibaud et al., "Characterization of dystrophic muscle in golden retriever muscular dystrophy dogs by nuclear magnetic resonance imaging," Abstract, *Neuromuscul. Disord.* 17(7):575-584, Jul. 2007, retrieved from https://www.ncbi.nlm.nih.gov/pubmed/17537632 on Dec. 14, 2016, 1 page.
Thibaud et al., "Comprehensive longitudinal characterization of canine muscular dystrophy by serial NMR imaging of GRMD dogs," Abstract, Neuromuscul. *Disord.* 22(S2):S85-S99, Oct. 2012, retrieved from https://www.ncbi.nlm.nih.gov/pubmed/?term=THIBAUD+2012++n . . . on Dec. 14, 2016, 1 page.
Thomas et al., "Recommendations for standards in transthoracic two-dimensional echocardiography in the dog and cat. Echocardiography Committee of the Specialty of Cardiology, American College of Veterinary Internal Medicine," Abstract, *J. Vet. Intern. Med.* 7(4):247-252, Jul.-Aug. 1993, retrieved from https://www.ncbi.nlm.nih.gov/pubmed/?term=American+college+of+veterinary+inter . . . on Dec. 15, 2016, 1 page.
Totomanoff et al., "Safety and Efficacy of Regional Intravenous (RI) Versus Intramuscular (IM) Delivery of rAAV1 and rAAV8 to Nonhuman Primate Skeletal Muscle," *Molecular Therapy* 16(7):1291-1299, Jul. 2008.
Wang et al., "Sustained AAV-mediated Dystrophin Expression in a Canine Model of Duchenne Muscular Dystrophy with a Brief Course of Immunosuppression," *Molecular Therapy* 15(6):1160-1166, Jun. 2007.
Wang et al., "Systemic Human Minidystrophin Gene Transfer Improves Functions and Life Span of Dystrophin and Dystrophin/Utrophin-Deficient Mice," *Journal of Orthopaedic Research* 27:421-429, Apr. 2009.
Wary et al., "Splitting of Pi and other $^{31}$P NMR anomalies of skeletal muscle metabolites in canine muscular dystrophy," Abstract, *NMR Biomed.* 25(10):1160-1169, Oct. 2012, retrieved from https://www.ncbi.nlm.nih.gov/pubmed/22354667 on Dec. 14, 2016, 1 page.
Zhang et al., "Dual AAV therapy ameliorates exercise-induced muscle injury and functional ischemia in murine models of Duchenne muscular dystrophy," *Human Molecular Genetics* 22(18):3720-3729, 2013.
Office Action for Australian Patent Application No. 2017200015, 4 pages, dated Feb. 1, 2018.
Office Action for Canadian Patent Application No. 2,953,187, 4 pages, dated Mar. 23, 2021.
Office Action for Canadian Patent Application No. 2,953,187, 4 pages, dated Mar. 18, 2022.
Office Action for Chinese Patent Application No. 2015800350987, 7 pages, dated Feb. 3, 2019.
Office Action for Chinese Patent Application No. 2015800350987, 8 pages, dated Nov. 1, 2019.
Office Action for Chinese Patent Application No. 2015800350987, 7 pages, dated Jul. 14, 2020.
Decision on Rejection for Chinese Patent Application No. 2015800350987, Partial English Translation, 3 pages, dated Feb. 2, 2021.
Office Action for European Patent Application No. 15731377.6, 7 pages, dated Sep. 12, 2016.
Summons to Attend Oral Proceedings for European Patent Application No. 15731377.6, 7 pages, dated May 12, 2017.
European Search Report for European Patent Application No. 14174848.3, 12 pages, dated Dec. 10, 2014.

(56) References Cited

OTHER PUBLICATIONS

European Search Report for European Patent Application No. 18175920.0, 15 pages, dated Aug. 18, 2023.
International Search Report and Written Opinion for PCT/EP2015/058964, 14 pages, dated Jul. 15, 2015.
International Search Report and Written Opinion for PCT/EP2015/064703, 15 pages, dated Sep. 4, 2015.
Office Action for Japanese Patent Application No. 2017-519971, 3 pages, dated Mar. 18, 2019.
Office Action for Japanese Patent Application No. 2021-049979, 5 pages, dated May 9, 2022.
Office Action for Japanese Patent Application No. 2021-049979, 5 pages, dated Dec. 19, 2022.
Denti et al., "Body-wide therapy of Duchenne muscular dystrophy in the mdx mouse model," *PNAS* 103(10):3758-3763 (Mar. 7, 2006).
Dickson et al., "235. Optimised AAV-Microdystrophin Gene Therapy in the GRMD Dog Model of Duchenne Muscular Dystrophy: Intravenous Delivery, Long-Term Expression, Functional Improvement and Absence of Adverse Cellular Immune Reactions," *Molecular Therapy* 22(Supplement 1):S89, 1 page (May 2014).
Duan, "Duchenne muscular dystrophy gene therapy: Lost in translation?" *Research and Reports in Biology* 2:31-42 (2011).
Hiroyuki Nakai, "Rapidly evolving adeno-associated virus vectors: increasing possibility of gene therapy with custom-made vectors," *Drug Delivery System* 24(6):582-591 (2009).
Kornegay et al., "Widespread Muscle Expression of an AAVP Human Mini-dystrophin Vector After Intravenous Injection in Neonatal Dystrophin-deficient Dogs," *Molecular Therapy* 18(8):1501-1508 (Aug. 2010).
Li et al., "172. Muscle Force Improvement by Long-Term Systemic Expression of an AAV9 Minidystrophin after Delivery in Young Adult GRMD Dogs without Immune Suppression," *Molecular Therapy* 20(Supplement 1):S69, 1 page (May 2012).
Miyake et al., "Neonatal systemic gene therapy for metachromatic leukodystrophy," Poster, 1 page (Mar. 18, 2019).
Shin et al., "Microdystrophin Ameliorates Muscular Dystrophy in the Canine Model of Duchenne Muscular Dystrophy," www.moleculartherapy.org 21(4):750-757 (Apr. 2013).
Wang et al., "Adeno-associated virus serotype 8 efficiently delivers genes to muscle and heart," *Nature Biotechnology* 23(3):321-328 (Mar. 2005).
Written Submission in Preparation To-During Oral Proceedings for European Application No. EP 15731377.6, 188 pages, dated Oct. 27, 2017, Caroline LeGuiner.
Minutes of Oral Proceedings for European Application No. EP 15731377.6, 7 pages, dated Dec. 15, 2017, David Sitch.

\* cited by examiner

SEQUENCE LISTING

```
<160> NUMBER OF SEQ ID NOS: 8

<210> SEQ ID NO 1
<211> LENGTH: 4640
<212> TYPE: DNA
<213> ORGANISM: Artificial Sequence
<220> FEATURE:
<223> OTHER INFORMATION: AAV_ITR_Spc512-human MD1

<400> SEQUENCE: 1
gcgcgctcgc tcgctcactg aggccgcccg ggcaaagccc gggcgtcggg cgacctttgg      60
tcgcccggcc tcagtgagcg agcgagcgcg cagagaggga gtggccaact ccatcactag     120
gggttccttg tagttaatga ttaacccgcc atgctactta tctacgtagc catgctctag     180
acatggctcg acagatcgag ctccaccgcg gtggcggccg tccgccctcg gcaccatcct     240
cacgacaccc aaatatggcg acgggtgagg aatggtgggg agttattttt agagcggtga     300
ggaaggtggg caggcagcag gtgttggcgc tctaaaaata actcccggga gttatttta     360 gagcggagga atggtggaca cccaaatatg gcgacggttc ctcacccgtc gccatatttg     420
ggtgtccgcc ctcggccggg gccgcattcc tgggggccgg gcggtgctcc cgcccgcctc     480
gataaaaggc tccggggccg gcggcggccc acgagctacc cggaggagcg ggaggcgcca     540
agctctagaa ctagtggatc ccccgggctg caggaattcg ccaccatgct gtggtgggag     600
gaagtggagg actgctacga gagagaggac gtgcagaaga aaaccttcac caagtgggtg     660
aacgcccagt tcagcaagtt cggcaagcag cacatcgaga acctgttcag cgacctgcag     720
gatggcagga gactgctgga tctgctggag ggactgaccg gccagaagct gcccaaggag     780
aagggcagca ccagagtgca cgccctgaac aacgtgaaca aggccctgag agtgctgcag     840
aacaacaacg tggacctggt gaatatcggc agcaccgaca tcgtggacgg caaccacaag     900 ctgacccctgg gcctgatctg gaacatcatc ctgcactggc aggtgaagaa cgtgatgaag     960
aacatcatgg ccggcctgca gcagaccaac agcgagaaga tcctgctgag ctgggtgagg    1020
cagagcacca gaaactaccc ccaggtgaac gtgatcaact tcaccacctc ctggagcgac    1080
ggcctggccc tgaacgccct gatccacagc cacagacccg acctgttcga ctggaacagc    1140
gtggtgtgtc agcagagcgc cacccagaga ctggagcacg ccttcaacat cgccagatac    1200
cagctgggca tcgagaagct gctggacccc gaggacgtgg acaccaccta ccccgacaag    1260
aaaagcatcc tgatgtatat tacctctctg tttcaggtgc tgccccagca ggtgtccatc    1320
gaggccatcc aggaagtgga aatgctgccc aggcccccca agtgaccaa ggaggagcac    1380 ttccagctgc accaccagat gcactatagc cagcagatca ccgtgtccct ggcccagggc    1440
tatgagagaa ccagcagccc caagcccaga ttcaagagct acgcctacac ccaggccgcc    1500
tacgtgacca cctccgaccc caccagaagc ccttcccca gccagcacct ggaggccccc    1560
gaggacaaga gcttcggcag cagcctgatg gagagcgaag tgaacctgga cagataccag    1620
accgccctgg aggaagtgct gtcttggctg ctgtccgccg aggacaccct gcaggcccag    1680
ggcgagatca gcaacgacgt ggaagtggtg aaggaccagt tccacaccca cgagggctac    1740
```

```
atgatggatc tgaccgccca ccagggcaga gtgggcaata tcctgcagct gggcagcaag   1800
ctgatcggca ccggcaagct gagcgaggac gaggagaccg aagtgcagga gcagatgaac   1860
ctgctgaaca gcagatggga gtgcctgaga gtggccagca tggagaagca gagcaacctg   1920
caccgcgtgc tgatggacct gcagaaccag aagctgaagg agctgaacga ctggctgacc   1980
aagaccgagg agcggaccag aaagatggag gaggagcccc tgggccccga cctggaggac   2040
ctgaagagac aggtgcagca gcacaaagtg ctgcaggagg acctggaaca ggagcaggtg   2100
cgcgtgaaca gcctgaccca catggtggtc gtggtggacg agagcagcgg cgaccacgcc   2160
acagccgccc tggaagagca gctgaaagtg ctgggcgaca gatgggccaa catctgccgg   2220
tggaccgagg acagatgggt gctgctgcag gacatcctgc tgaagtggca gagactgaca   2280
gaggagcagt gcctgtttag cgcctggctg agcgagaagg aggacgccgt gaacaagatc   2340
cacaccaccg gcttcaagga ccagaacgag atgctgagca gcctgcagaa gctggccgtg   2400
ctgaaggccg atctggagaa gaaaaagcag agcatgggca agctgtactc cctgaagcag   2460
gacctgctgt ccaccctgaa gaacaagagc gtgacccaga aaaccgaggc ctggctggac   2520
aatttcgccc ggtgctggga caatctggtg cagaaactgg agaagagcac cgcccagatc   2580
agccaggccg tgaccaccac ccagcccagc ctgacacaga ccaccgtgat ggagaccgtg   2640
accacagtga ccaccaggga gcagatcctg tgaagcacg cccaggagga gctgccccct   2700
ccccccctc agaagaagcg gcagatcaca gtggacaccc tggagagact gcaggagctg   2760
caggaagcca ccgacgagct ggacctgaag ctgagacagg ccgaagtgat caagggcagc   2820
tggcagcctg tgggcgatct gctgatcgac agcctgcagg accacctgga gaaagtgaag   2880
gccctgcggg gcgagatcgc cccccctgaag gagaatgtga ccacgtgaa cgacctggcc   2940
agacagctga ccaccctggg catccagctg agccccctaca atctgagcac cctggaagat   3000
ctgaacaccc ggtggaaact gctgcaggtg gccgtggagg atagagtgag gcagctgcac   3060
gaggcccaca gagacttcgg ccctgcctcc cagcacttcc tgagcaccag cgtgcagggc   3120
ccctgggaga gagccatctc ccccaacaaa gtgccctact acatcaacca cgagacccag   3180
accacctgct gggaccaccc taagatgacc gagctgtacc agagcctggc cgacctgaac   3240
aatgtgcggt tcagcgccta cagaaccgcc atgaagctgc ggagactgca gaaggccctg   3300
tgcctggacc tgctgagcct gagcgccgcc tgcgacgccc tggaccagca aacctgaag   3360
cagaacgacc agcccatgga cattctgcag atcatcaact gcctgaccac catctacgat   3420
cggctggagc aggagcacaa caacctggtg aacgtgcccc tgtgcgtgga catgtgcctg   3480
aattggctgc tgaacgtgta cgacaccggc aggaccggca gaatcagagt gctgtccttc   3540
aagaccggca tcatcagcct gtgcaaggcc cacctggagg ataagtaccg ctacctgttc   3600
aagcaggtgg ccagcagcac cggcttctgc gatcagagga gactgggcct gctgctgcac   3660
gatagcatcc agatccctag gcagctgggc gaagtggcca gctttggcgg cagcaacatc   3720
gagccctctg tgaggagctg cttccagttc gccaacaaca gcccgagat cgaggccgcc   3780
ctgttcctgg attggatgag gctggagccc cagagcatgg tgtggctgcc tgtgctgcac   3840
agagtggccc ccgccgagac cgccaagcac caggccaagt gcaacatctg caaggagtgc   3900
cccatcatcg gcttccggta caggagcctg aagcacttca actacgacat ctgccagagc   3960
tgcttttttca gcggcagagt ggccaagggc cacaagatgc actacccat ggtggagtac   4020
tgcacccca ccacctccgg cgaggatgtg agagacttcg ccaaagtgct gaagaataag   4080
```

| | |
|---|---|
| ttccggacca agcggtactt tgccaagcac cccaggatgg gctacctgcc cgtgcagacc | 4140 |
| gtgctggagg gcgacaacat ggagaccgac accatgtgat gatgagcggc cgcttccctt | 4200 |
| tagtgagggt taatgcttcg agcagacatg ataagataca ttgatgagtt tggacaaacc | 4260 |
| acaactagaa tgcagtgaaa aaaatgcttt atttgtgaaa tttgtgatgc tattgcttta | 4320 |
| tttgtaacca ttataagctg caataaacaa gttaacaaca caattgcat tcattttatg | 4380 |
| tttcaggttc agggggagat gtgggaggtt ttttaaagca agtaaaacct ctacaaatgt | 4440 |
| ggtaaaatcc gataaggact agagcatggc tacgtagata agtagcatgg cgggttaatc | 4500 |
| attaactaca aggaacccct agtgatgag ttggccactc cctctctgcg cgctcgctcg | 4560 |
| ctcactgagg ccgggcgacc aaaggtcgcc cgacgcccgg gctttgcccg gcggcctca | 4620 |
| gtgagcgagc gagcgcgcag | 4640 |

<210> SEQ ID NO 2
<211> LENGTH: 4643
<212> TYPE: DNA
<213> ORGANISM: Artificial Sequence
<220> FEATURE:
<223> OTHER INFORMATION: AAV_ITR_Spc512-canine MD1

<400> SEQUENCE: 2

| | |
|---|---|
| gcgcgctcgc tcgctcactg aggccgcccg ggcaaagccc gggcgtcggg cgacctttgg | 60 |
| tcgcccggcc tcagtgagcg agcgagcgcg cagagaggga gtggccaact ccatcactag | 120 |
| gggttccttg tagttaatga ttaacccgcc atgctactta tctacgtagc catgctctag | 180 |
| acatggctcg acagatcgag ctccaccgcg gtggcggccg tccgccctcg gcaccatcct | 240 |
| cacgacaccc aaatatggcg acgggtgagg aatggtgggg agttattttt agagcggtga | 300 |
| ggaaggtggg caggcagcag gtgttggcgc tctaaaaata actcccggga gttattttta | 360 |
| gagcggagga atggtggaca cccaaatatg gcgacggttc ctcacccgtc gccatatttg | 420 |
| ggtgtccgcc ctcggccggg gccgcattcc tgggggccgg gcggtgctcc cgcccgcctc | 480 |
| gataaaaggc tccggggccg gcggcggccc acgagctacc cggaggagcg ggaggcgcca | 540 |
| agctctagaa ctagtggatc ccccgggctg caggaattcg ccaccatgct gtggtgggag | 600 |
| gaagtggagg actgctacga gagagaggac gtgcagaaga aaaccttcac caagtggatc | 660 |
| aacgcccagt tcagcaagtt cggcaagcag cacatcgaga acctgttcag cgatctgcag | 720 |
| gatggcagga gactgctgga tctgctggag ggactgaccg gccagaagct gcccaaggag | 780 |
| aagggcagca ccagagtgca cgccctgaac aacgtgaaca aggccctgag agtgctgcag | 840 |
| aagaacaacg tggacctggt ggatatcggc agcaccgaca tcgtggacgg caaccacaag | 900 |
| ctgacccctg gcctgatctg gaacatcatc ctgcactggc aggtgaagaa cgtgatgaag | 960 |
| aacatcatgg ccggcctgca gcagaccaac agcgagaaga tcctgctgag ctgggtgagg | 1020 |
| cagagcacca gaaactaccc ccaggtgaac gtgatcaact tcaccacctc ctggagcgac | 1080 |
| ggcctggccc tgaacgccct gatccacagc cacagacccg acctgttcga ctggaacagc | 1140 |
| gtggtgtgtc agcagagcgc cacccagaga ctggagcacg ccttcaacat cgccaagtac | 1200 |
| cagctgggca tcgagaagct gctggacccc gaggacgtgg ccaccaccta ccccgacaag | 1260 |
| aaaagcatcc tgatgtatat taccagcctg ttccaggtgc tgccccagca ggtgtccatc | 1320 |
| gaggccatcc aggaagtgga aatgctgccc aggcccagca agtgaccag ggaggagcac | 1380 |
| ttccagctgc accaccagat gcactatagc cagcagatca ccgtgtccct ggcccagggc | 1440 |
| tatgagagag cccctagcag ccccaagccc cggttcaaga gctacgccta cacccaggcc | 1500 |

```
gcctacgtga ccacctccga ccccaccaga agcccctgc ccagccagca cctggagacc   1560
cctgaggata agagcttcgg cagaagcctg accgagaccg aggccaacct ggatagctac   1620
cagaccgccc tggaggaagt gctgtcttgg ctgctgtccg ccgaggacgc cctgcaggcc   1680
cagggcgaga tcagcaacga cgtggaagaa gtgaaggagc agttccacac ccacgagggc   1740
tacatgatgg acctgaccag ccaccagggc agagtgggca acgtgctgca gctgggcagc   1800
cagctgatcg gcaccggcaa gctgagcgag gacgaggaga ccgaagtgca ggaacagatg   1860
aacctgctga cagcagatg ggagtgcctg agagtggcca gcatggagaa gcagagcaac   1920
ctgcacaaag tgctgatgga tctgcagaac cagcagctga aggagctgaa cgactggctg   1980
accaagacag aggagcggac ccggaagatg agaaggagc ccctgggccc tgacatcgag   2040
gacctgaaga ggcaggtgca gcagcataag gtcctgcagg aggatctgga gcaggagcag   2100
gtgcgcgtga acagcctgac ccacatggtg gtcgtggtgg acgagagcag cggcgaccac   2160
gccacagccg ccctggaaga gcagctgaaa gtgctgggcg gcagatgggc caatatctgc   2220
cggtggaccg aggacagatg ggtgctgctg caggacatcc tgctgaagtg cagagattc   2280 accgaggagc agtgcctgtt tagcgcctgg ctgagcgaga aggaggacgc cgtgaacaag   2340
atccacacca ccggcttcaa ggaccagagc gaagtgctgt ccaacctgca gaagctggcc   2400
gtgctgaaaa ccgacctgga gaagaaaaag cagaccatgg acaagctgtg cagcctgaac   2460
caggacctgc tgagcgccct gaagaacacc gtggtggccc acaagatgga ggcctggctg   2520
gataatagcg ctcagagatg ggataatctg gtgcagaaac tggagaagag cagcgcccag   2580
atcagccagg ccgtgaccac cacccagccc agcctgacac agaccaccgt gatggagacc   2640
gtgaccatgg tgaccaccag ggagcacatc ctggtgaagc acgcccagga ggagctgccc   2700 cctcccccc ctcagaagaa gcggcagatc atcgtggatg ccctggagag actgcaggag   2760
ctgcaggaag ccaccgacga gctggacctg aagctgagac aggccgaagt gatcaagggc   2820
agctggcagc ctgtgggcga tctgctgatc gacagcctgc aggaccacct ggagaaagtg   2880
aaggccctgc ggggcgagac cacccccctg aaggagaacg tgtcctacgt gaacgacctg   2940
gccagacagc tgaccaccct gggcattcag ctgagcccct acaacctgaa caccctggag   3000
gatctgaaca cccggtggaa actgctgcag gtggccattg aggaccggat caggcagctg   3060
cacgaggccc acagagactt cggccctgct tctcagcatt tcctgagcac cagcgtgcag   3120
ggcccctggg agagagccat cagccccaac aaagtgccct actacatcaa ccacgagacc   3180
cagaccacct gctgggacca ccctaagatg accgagctgt accagagcct ggccgacctg   3240
aacaatgtgc ggttcagcgc ctacagaacc gccatgaagc tgcggagact gcagaaggcc   3300
ctgtgcctga cctgctgtc cctgagcgcc gcctgcgacg ccctggacca gcacaacctg   3360
aagcagaacg accagcccat ggatatcctg caggtgatca actgcctgac caccatctac   3420
gatcggctgg agcaggagca caacaacctg gtgaacgtgc cctgtgcgt ggacatgtgc   3480 ctgaattggc tgctgaacgt gtacgacacc ggcaggaccg gcagaatcag agtgctgtcc   3540
ttcaagaccg gcatcatcag cctgtgcaag gcccacctgg aggataagta ccgctacctg   3600
ttcaagcagg tggccagcag caccggcttc tgcgatcaga ggagactggg cctgctgctg   3660
cacgatagca tccagatccc taggcagctg ggcgaagtgg ccagctttgg cggcagcaac   3720
atcgagccct ctgtgaggag ctgcttccag ttcgccaaca caagcccga gatcgaggcc   3780 gccctgttcc tggattggat gaggctggag ccccagagca tggtgtggct gcctgtgctg   3840
```

-continued

```
cacagagtgg ccgccgccga gaccgccaag caccaggcca agtgcaacat ctgcaaggag    3900
tgccccatca tcggcttccg gtacaggagc ctgaagcact tcaactacga catctgccag    3960
agctgctttt tcagcggcag agtggccaag ggccacaaga tgcactaccc catggtggag    4020
tactgcaccc ccaccacctc cggcgaggat gtgagagact cgccaaagt gctgaagaat     4080 aagttccgga ccaagcggta ctttgccaag cacccaggga tgggctacct gcccgtgcag    4140
accgtgctgg agggcgacaa catggagacc gacaccatgt gatgatgagc ggccgcttcc    4200
ctttagtgag ggttaatgct tcgagcagac atgataagat acattgatga gtttggacaa    4260
accacaacta gaatgcagtg aaaaaaatgc tttatttgtg aaatttgtga tgctattgct    4320
ttatttgtaa ccattataag ctgcaataaa caagttaaca acaacaattg cattcatttt    4380
atgtttcagg ttcaggggga gatgtgggag gttttttaaa gcaagtaaaa cctctacaaa    4440
tgtggtaaaa tccgataagg actagagcat ggctacgtag ataagtagca tggcgggtta    4500
atcattaact acaaggaacc cctagtgatg gagttggcca ctccctctct gcgcgctcgc    4560
tcgctcactg aggccgggcg accaaaggtc gcccgacgcc cgggctttgc ccgggcggcc    4620
tcagtgagcg agcgagcgcg cag                                            4643
```

<210> SEQ ID NO 3
<211> LENGTH: 1197
<212> TYPE: PRT
<213> ORGANISM: Artificial Sequence
<220> FEATURE:
<223> OTHER INFORMATION: human MD1

<400> SEQUENCE: 3

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220
```

```
Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
            245                 250                 255

Pro Pro Lys Val Thr Lys Glu Glu His Phe Gln Leu His His Gln Met
        260                 265                 270

His Tyr Ser Gln Gln Ile Thr Val Ser Leu Ala Gln Gly Tyr Glu Arg
    275                 280                 285

Thr Ser Ser Pro Lys Pro Arg Phe Lys Ser Tyr Ala Tyr Thr Gln Ala
290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
            325                 330                 335

Ser Glu Val Asn Leu Asp Arg Tyr Gln Thr Ala Leu Glu Glu Val Leu
        340                 345                 350

Ser Trp Leu Leu Ser Ala Glu Asp Thr Leu Gln Ala Gln Gly Glu Ile
    355                 360                 365

Ser Asn Asp Val Glu Val Val Lys Asp Gln Phe His Thr His Glu Gly
370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
            405                 410                 415

Glu Thr Glu Val Gln Glu Gln Met Asn Leu Leu Asn Ser Arg Trp Glu
        420                 425                 430

Cys Leu Arg Val Ala Ser Met Glu Lys Gln Ser Asn Leu His Arg Val
    435                 440                 445

Leu Met Asp Leu Gln Asn Gln Lys Leu Lys Glu Leu Asn Asp Trp Leu
450                 455                 460

Thr Lys Thr Glu Glu Arg Thr Arg Lys Met Glu Glu Glu Pro Leu Gly
465                 470                 475                 480

Pro Asp Leu Glu Asp Leu Lys Arg Gln Val Gln Gln His Lys Val Leu
            485                 490                 495

Gln Glu Asp Leu Glu Gln Glu Gln Val Arg Val Asn Ser Leu Thr His
        500                 505                 510

Met Val Val Val Asp Glu Ser Ser Gly Asp His Ala Thr Ala Ala
    515                 520                 525

Leu Glu Glu Gln Leu Lys Val Leu Gly Asp Arg Trp Ala Asn Ile Cys
530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
            565                 570                 575

Glu Lys Glu Asp Ala Val Asn Lys Ile His Thr Thr Gly Phe Lys Asp
        580                 585                 590

Gln Asn Glu Met Leu Ser Ser Leu Gln Lys Leu Ala Val Leu Lys Ala
    595                 600                 605

Asp Leu Glu Lys Lys Lys Gln Ser Met Gly Lys Leu Tyr Ser Leu Lys
610                 615                 620

Gln Asp Leu Leu Ser Thr Leu Lys Asn Lys Ser Val Thr Gln Lys Thr
625                 630                 635                 640
```

-continued

Glu Ala Trp Leu Asp Asn Phe Ala Arg Cys Trp Asp Asn Leu Val Gln
                645                 650                 655

Lys Leu Glu Lys Ser Thr Ala Gln Ile Ser Gln Ala Val Thr Thr Thr
            660                 665                 670

Gln Pro Ser Leu Thr Gln Thr Thr Val Met Glu Thr Val Thr Thr Val
        675                 680                 685

Thr Thr Arg Glu Gln Ile Leu Val Lys His Ala Gln Glu Glu Leu Pro
690                 695                 700

Pro Pro Pro Gln Lys Lys Arg Gln Ile Thr Val Asp Thr Leu Glu
705                 710                 715                 720

Arg Leu Gln Glu Leu Gln Glu Ala Thr Asp Glu Leu Asp Leu Lys Leu
                725                 730                 735

Arg Gln Ala Glu Val Ile Lys Gly Ser Trp Gln Pro Val Gly Asp Leu
            740                 745                 750

Leu Ile Asp Ser Leu Gln Asp His Leu Glu Lys Val Lys Ala Leu Arg
        755                 760                 765

Gly Glu Ile Ala Pro Leu Lys Glu Asn Val Ser His Val Asn Asp Leu
770                 775                 780

Ala Arg Gln Leu Thr Thr Leu Gly Ile Gln Leu Ser Pro Tyr Asn Leu
785                 790                 795                 800

Ser Thr Leu Glu Asp Leu Asn Thr Arg Trp Lys Leu Leu Gln Val Ala
            805                 810                 815

Val Glu Asp Arg Val Arg Gln Leu His Glu Ala His Arg Asp Phe Gly
        820                 825                 830

Pro Ala Ser Gln His Phe Leu Ser Thr Ser Val Gln Gly Pro Trp Glu
        835                 840                 845

Arg Ala Ile Ser Pro Asn Lys Val Pro Tyr Tyr Ile Asn His Glu Thr
        850                 855                 860

Gln Thr Thr Cys Trp Asp His Pro Lys Met Thr Glu Leu Tyr Gln Ser
865                 870                 875                 880

Leu Ala Asp Leu Asn Asn Val Arg Phe Ser Ala Tyr Arg Thr Ala Met
                885                 890                 895

Lys Leu Arg Arg Leu Gln Lys Ala Leu Cys Leu Asp Leu Leu Ser Leu
            900                 905                 910

Ser Ala Ala Cys Asp Ala Leu Asp Gln His Asn Leu Lys Gln Asn Asp
        915                 920                 925

Gln Pro Met Asp Ile Leu Gln Ile Ile Asn Cys Leu Thr Thr Ile Tyr
        930                 935                 940

Asp Arg Leu Glu Gln Glu His Asn Asn Leu Val Asn Val Pro Leu Cys
945                 950                 955                 960

Val Asp Met Cys Leu Asn Trp Leu Leu Asn Val Tyr Asp Thr Gly Arg
                965                 970                 975

Thr Gly Arg Ile Arg Val Leu Ser Phe Lys Thr Gly Ile Ile Ser Leu
            980                 985                 990

Cys Lys Ala His Leu Glu Asp Lys Tyr Arg Tyr Leu Phe Lys Gln Val
        995                 1000                1005

Ala Ser Ser Thr Gly Phe Cys Asp Gln Arg Arg Leu Gly Leu Leu Leu
    1010                1015                1020

His Asp Ser Ile Gln Ile Pro Arg Gln Leu Gly Glu Val Ala Ser Phe
1025                1030                1035                1040

Gly Gly Ser Asn Ile Glu Pro Ser Val Arg Ser Cys Phe Gln Phe Ala
                1045                1050                1055

Asn Asn Lys Pro Glu Ile Glu Ala Ala Leu Phe Leu Asp Trp Met Arg

-continued

```
               1060                1065                1070

Leu Glu Pro Gln Ser Met Val Trp Leu Pro Val Leu His Arg Val Ala
        1075                1080                1085

Ala Ala Glu Thr Ala Lys His Gln Ala Lys Cys Asn Ile Cys Lys Glu
    1090                1095                1100

Cys Pro Ile Ile Gly Phe Arg Tyr Arg Ser Leu Lys His Phe Asn Tyr
1105                1110                1115                1120

Asp Ile Cys Gln Ser Cys Phe Phe Ser Gly Arg Val Ala Lys Gly His
                1125                1130                1135

Lys Met His Tyr Pro Met Val Glu Tyr Cys Thr Pro Thr Thr Ser Gly
            1140                1145                1150

Glu Asp Val Arg Asp Phe Ala Lys Val Leu Lys Asn Lys Phe Arg Thr
        1155                1160                1165

Lys Arg Tyr Phe Ala Lys His Pro Arg Met Gly Tyr Leu Pro Val Gln
    1170                1175                1180

Thr Val Leu Glu Gly Asp Asn Met Glu Thr Asp Thr Met
1185                1190                1195

<210> SEQ ID NO 4
<211> LENGTH: 1198
<212> TYPE: PRT
<213> ORGANISM: Artificial Sequence
<220> FEATURE:
<223> OTHER INFORMATION: canine MD1

<400> SEQUENCE: 4

Met Leu Trp Trp Glu Glu Val Glu Asp Cys Tyr Glu Arg Glu Asp Val
1               5                   10                  15

Gln Lys Lys Thr Phe Thr Lys Trp Ile Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Lys Asn Asn Val Asp Leu Val Asp Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Lys Tyr Gln Leu Gly
        195                 200                 205

Ile Glu Lys Leu Leu Asp Pro Glu Asp Val Ala Thr Thr Tyr Pro Asp
    210                 215                 220

Lys Lys Ser Ile Leu Met Tyr Ile Thr Ser Leu Phe Gln Val Leu Pro
```

-continued

```
            225                 230                 235                 240
Gln Gln Val Ser Ile Glu Ala Ile Gln Glu Val Glu Met Leu Pro Arg
                245                 250                 255

Pro Ser Lys Val Thr Arg Glu Glu His Phe Gln Leu His His Gln Met
                260                 265                 270

His Tyr Ser Gln Gln Ile Thr Val Ser Leu Ala Gln Gly Tyr Glu Arg
                275                 280                 285

Ala Pro Ser Ser Pro Lys Pro Arg Phe Lys Ser Tyr Ala Tyr Thr Gln
            290                 295                 300

Ala Ala Tyr Val Thr Thr Ser Asp Pro Thr Arg Ser Pro Leu Pro Ser
305                 310                 315                 320

Gln His Leu Glu Thr Pro Glu Asp Lys Ser Phe Gly Arg Ser Leu Thr
                    325                 330                 335

Glu Thr Glu Ala Asn Leu Asp Ser Tyr Gln Thr Ala Leu Glu Glu Val
                340                 345                 350

Leu Ser Trp Leu Leu Ser Ala Glu Asp Ala Leu Gln Ala Gln Gly Glu
                355                 360                 365

Ile Ser Asn Asp Val Glu Val Lys Glu Gln Phe His Thr His Glu
            370                 375                 380

Gly Tyr Met Met Asp Leu Thr Ser His Gln Gly Arg Val Gly Asn Val
385                 390                 395                 400

Leu Gln Leu Gly Ser Gln Leu Ile Gly Thr Gly Lys Leu Ser Glu Asp
                    405                 410                 415

Glu Glu Thr Glu Val Gln Glu Gln Met Asn Leu Leu Asn Ser Arg Trp
                420                 425                 430

Glu Cys Leu Arg Val Ala Ser Met Glu Lys Gln Ser Asn Leu His Lys
                435                 440                 445

Val Leu Met Asp Leu Gln Asn Gln Gln Leu Lys Glu Leu Asn Asp Trp
            450                 455                 460

Leu Thr Lys Thr Glu Glu Arg Thr Arg Lys Met Glu Lys Glu Pro Leu
465                 470                 475                 480

Gly Pro Asp Ile Glu Asp Leu Lys Arg Gln Val Gln Gln His Lys Val
                    485                 490                 495

Leu Gln Glu Asp Leu Glu Gln Glu Gln Val Arg Val Asn Ser Leu Thr
                500                 505                 510

His Met Val Val Val Asp Glu Ser Ser Gly Asp His Ala Thr Ala
            515                 520                 525

Ala Leu Glu Glu Gln Leu Lys Val Leu Gly Gly Arg Trp Ala Asn Ile
            530                 535                 540

Cys Arg Trp Thr Glu Asp Arg Trp Val Leu Leu Gln Asp Ile Leu Leu
545                 550                 555                 560

Lys Trp Gln Arg Phe Thr Glu Glu Gln Cys Leu Phe Ser Ala Trp Leu
                    565                 570                 575

Ser Glu Lys Glu Asp Ala Val Asn Lys Ile His Thr Thr Gly Phe Lys
                580                 585                 590

Asp Gln Ser Glu Val Leu Ser Asn Leu Gln Lys Leu Ala Val Leu Lys
            595                 600                 605

Thr Asp Leu Glu Lys Lys Gln Thr Met Asp Lys Leu Cys Ser Leu
            610                 615                 620

Asn Gln Asp Leu Leu Ser Ala Leu Lys Asn Thr Val Ala His Lys
625                 630                 635                 640

Met Glu Ala Trp Leu Asp Asn Ser Ala Gln Arg Trp Asp Asn Leu Val
                    645                 650                 655
```

-continued

```
Gln Lys Leu Glu Lys Ser Ser Ala Gln Ile Ser Gln Ala Val Thr Thr
            660                 665                 670

Thr Gln Pro Ser Leu Thr Gln Thr Thr Val Met Glu Thr Val Thr Met
        675                 680                 685

Val Thr Thr Arg Glu His Ile Leu Val Lys His Ala Gln Glu Glu Leu
    690                 695                 700

Pro Pro Pro Pro Pro Gln Lys Lys Arg Gln Ile Ile Val Asp Ala Leu
705                 710                 715                 720

Glu Arg Leu Gln Glu Leu Gln Glu Ala Thr Asp Glu Leu Asp Leu Lys
                725                 730                 735

Leu Arg Gln Ala Glu Val Ile Lys Gly Ser Trp Gln Pro Val Gly Asp
            740                 745                 750

Leu Leu Ile Asp Ser Leu Gln Asp His Leu Glu Lys Val Lys Ala Leu
        755                 760                 765

Arg Gly Glu Thr Thr Pro Leu Lys Glu Asn Val Ser Tyr Val Asn Asp
    770                 775                 780

Leu Ala Arg Gln Leu Thr Thr Leu Gly Ile Gln Leu Ser Pro Tyr Asn
785                 790                 795                 800

Leu Asn Thr Leu Glu Asp Leu Asn Thr Arg Trp Lys Leu Leu Gln Val
                805                 810                 815

Ala Ile Glu Asp Arg Ile Arg Gln Leu His Glu Ala His Arg Asp Phe
            820                 825                 830

Gly Pro Ala Ser Gln His Phe Leu Ser Thr Ser Val Gln Gly Pro Trp
        835                 840                 845

Glu Arg Ala Ile Ser Pro Asn Lys Val Pro Tyr Tyr Ile Asn His Glu
    850                 855                 860

Thr Gln Thr Thr Cys Trp Asp His Pro Lys Met Thr Glu Leu Tyr Gln
865                 870                 875                 880

Ser Leu Ala Asp Leu Asn Asn Val Arg Phe Ser Ala Tyr Arg Thr Ala
                885                 890                 895

Met Lys Leu Arg Arg Leu Gln Lys Ala Leu Cys Leu Asp Leu Leu Ser
            900                 905                 910

Leu Ser Ala Ala Cys Asp Ala Leu Asp Gln His Asn Leu Lys Gln Asn
        915                 920                 925

Asp Gln Pro Met Asp Ile Leu Gln Val Ile Asn Cys Leu Thr Thr Ile
    930                 935                 940

Tyr Asp Arg Leu Glu Gln Glu His Asn Asn Leu Val Asn Val Pro Leu
945                 950                 955                 960

Cys Val Asp Met Cys Leu Asn Trp Leu Leu Asn Val Tyr Asp Thr Gly
                965                 970                 975

Arg Thr Gly Arg Ile Arg Val Leu Ser Phe Lys Thr Gly Ile Ile Ser
            980                 985                 990

Leu Cys Lys Ala His Leu Glu Asp Lys Tyr Arg Tyr Leu Phe Lys Gln
        995                 1000                1005

Val Ala Ser Ser Thr Gly Phe Cys Asp Gln Arg Arg Leu Gly Leu Leu
    1010                1015                1020

Leu His Asp Ser Ile Gln Ile Pro Arg Gln Leu Gly Glu Val Ala Ser
1025                1030                1035                1040

Phe Gly Gly Ser Asn Ile Glu Pro Ser Val Arg Ser Cys Phe Gln Phe
                1045                1050                1055

Ala Asn Asn Lys Pro Glu Ile Glu Ala Ala Leu Phe Leu Asp Trp Met
            1060                1065                1070
```

Arg Leu Glu Pro Gln Ser Met Val Trp Leu Pro Val Leu His Arg Val
    1075                1080                1085

Ala Ala Ala Glu Thr Ala Lys His Gln Ala Lys Cys Asn Ile Cys Lys
    1090                1095                1100

Glu Cys Pro Ile Ile Gly Phe Arg Tyr Arg Ser Leu Lys His Phe Asn
1105                1110                1115                1120

Tyr Asp Ile Cys Gln Ser Cys Phe Phe Ser Gly Arg Val Ala Lys Gly
            1125                1130                1135

His Lys Met His Tyr Pro Met Val Glu Tyr Cys Thr Pro Thr Thr Ser
                1140                1145                1150

Gly Glu Asp Val Arg Asp Phe Ala Lys Val Leu Lys Asn Lys Phe Arg
    1155                1160                1165

Thr Lys Arg Tyr Phe Ala Lys His Pro Arg Met Gly Tyr Leu Pro Val
    1170                1175                1180

Gln Thr Val Leu Glu Gly Asp Asn Met Glu Thr Asp Thr Met
1185                1190                1195

<210> SEQ ID NO 5
<211> LENGTH: 3600
<212> TYPE: DNA
<213> ORGANISM: Artificial Sequence
<220> FEATURE:
<223> OTHER INFORMATION: opt human MD1

<400> SEQUENCE: 5

```
atgctgtggt gggaggaagt ggaggactgc tacgagagag aggacgtgca gaagaaaacc      60
ttcaccaagt gggtgaacgc ccagttcagc aagttcggca gcagcacat cgagaacctg     120
ttcagcgacc tgcaggatgg caggagactg ctggatctgc tggagggact gaccggccag     180
aagctgccca ggagaagggg cagcaccaga gtgcacgccc tgaacaacgt gaacaaggcc     240
ctgagagtgc tgcagaacaa caacgtggac ctggtgaata tcggcagcac cgacatcgtg     300
gacggcaacc acaagctgac cctgggcctg atctggaaca tcatcctgca ctggcaggtg     360
aagaacgtga tgaagaacat catggccggc ctgcagcaga ccaacagcga agatcctg      420
ctgagctggg tgaggcagag caccagaaac taccccagg tgaacgtgat caacttcacc     480
acctcctgga gcgacggcct ggccctgaac gccctgatcc acagccacag acccgacctg     540
ttcgactgga cagcgtggt gtgtcagcag agcgccaccc agagactgga gcacgccttc     600
aacatcgcca gataccagct gggcatcgag aagctgctgg accccgagga cgtggacacc     660
acctaccccg acaagaaaag catcctgatg tatattacct ctctgtttca ggtgctgccc     720
cagcaggtgt ccatcgaggc catccaggaa gtggaaatgc tgcccaggcc ccccaaagtg     780
accaaggagg agcacttcca gctgcaccac cagatgcact atagccagca gatcaccgtg     840
tccctggccc agggctatga gagaaccagc agccccaagc cagattcaa gagctacgcc     900
tacacccagg ccgcctacgt gaccacctcc gaccccacca gaagcccctt ccccagccag     960
cacctggagg ccccgagga caagagcttc ggcagcagcc tgatggagag cgaagtgaac    1020
ctggacagat accagaccgc cctggaggaa gtgctgtctt ggctgctgtc cgccgaggac    1080
accctgcagg cccagggcga gatcagcaac gacgtgaag tggtgaagga ccagttccac    1140
acccacgagg gctacatgat ggatctgacc gcccaccagg gcagagtggg caatatcctg    1200
cagctgggca gcaagctgat cggcaccggc aagctgagcg aggacgagga gaccgaagtg    1260
caggagcaga tgaacctgct gaacagcaga tgggagtgcc tgagagtggc cagcatggag    1320
aagcagagca acctgcaccg cgtgctgatg gacctgcaga accagaagct gaaggagctg    1380
```

```
aacgactggc tgaccaagac cgaggagcgg accagaaaga tggaggagga gcccctgggc    1440
cccgacctgg aggacctgaa gagacaggtg cagcagcaca aagtgctgca ggaggacctg    1500
gaacaggagc aggtgcgcgt gaacagcctg acccacatgg tggtcgtggt ggacgagagc    1560
agcggcgacc acgccacagc cgccctggaa gagcagctga aagtgctggg cgacagatgg    1620
gccaacatct gccggtggac cgaggacaga tgggtgctgc tgcaggacat cctgctgaag    1680
tggcagagac tgacagagga gcagtgcctg tttagcgcct ggctgagcga aggaggac    1740 gccgtgaaca agatccacac caccggcttc aaggaccaga cgagatgct gagcagcctg    1800 cagaagctgg ccgtgctgaa ggccgatctg agaagaaaa agcagagcat gggcaagctg    1860
tactccctga gcaggacct gctgtccacc ctgaagaaca gagcgtgac ccagaaaacc    1920 gaggcctggc tggacaattt cgccggtgc tgggacaatc tggtgcagaa actggagaag    1980
agcaccgccc agatcagcca ggccgtgacc accacccagc ccagcctgac acagaccacc    2040
gtgatggaga ccgtgaccac agtgaccacc agggagcaga tcctggtgaa gcacgcccag    2100
gaggagctgc cccctccccc ccctcagaag aagcggcaga tcacagtgga caccctggag    2160
agactgcagg agctgcagga agccaccgac gagctggacc tgaagctgag acaggccgaa    2220
gtgatcaagg gcagctggca gcctgtgggc gatctgctga tcgacagcct gcaggaccac    2280
ctggagaaag tgaaggccct gcggggcgag atcgccccc tgaaggagaa tgtgagccac    2340
gtgaacgacc tggccagaca gctgaccacc ctgggcatcc agctgagccc ctacaatctg    2400
agcaccctgg aagatctgaa cacccggtgg aaactgctgc aggtggccgt ggaggataga    2460
gtgaggcagc tgcacgaggc ccacagagac ttcggccctg cctcccagca cttcctgagc    2520
accagcgtgc agggccctg ggagagagc atctcccca acaaagtgcc ctactacatc    2580
aaccacgaga cccagaccac ctgctgggac caccctaaga tgaccgagct gtaccagagc    2640
ctggccgacc tgaacaatgt gcggttcagc gcctacagaa ccgccatgaa gctgcggaga    2700
ctgcagaagg ccctgtgcct ggacctgctg agcctgagcg ccgcctgcga cgccctggac    2760
cagcacaacc tgaagcagaa cgaccagccc atggacattc tgcagatcat caactgcctg    2820
accaccatct acgatcggct ggagcaggag cacaacaacc tggtgaacgt gcccctgtgc    2880
gtggacatgt gcctgaattg gctgctgaac gtgtacgaca ccggcaggac cggcagaatc    2940
agagtgctgt ccttcaagac cggcatcatc agcctgtgca aggcccacct ggaggataag    3000
taccgctacc tgttcaagca ggtggccagc agcaccggct tctgcgatca gaggagactg    3060
ggcctgctgc tgcacgatag catccagatc cctaggcagc tgggcgaagt ggccagcttt    3120
ggcggcagca acatcgagcc ctctgtgagg agctgcttcc agttcgccaa caacaagccc    3180
gagatcgagg ccgccctgtt cctggattgg atgaggctgg agcccagag catggtgtgg    3240 ctgcctgtgc tgcacagagt ggccgccgcc gagaccgcca agcaccaggc caagtgcaac    3300
atctgcaagg agtgccccat catcggcttc cggtacagga gcctgaagca cttcaactac    3360
gacatctgcc agagctgctt tttcagcggc agagtggcca agggccacaa gatgcactac    3420
cccatggtgg agtactgcac ccccaccacc tccggcgagg atgtgagaga cttcgccaaa    3480
gtgctgaaga ataagttccg gaccaagcgg tactttgcca agcaccccag gatgggctac    3540
ctgcccgtgc agaccgtgct ggagggcgac aacatggaga ccgacaccat gtgatgatga    3600
```

<210> SEQ ID NO 6
<211> LENGTH: 3603
<212> TYPE: DNA

<213> ORGANISM: Artificial Sequence
<220> FEATURE:
<223> OTHER INFORMATION: opt canine MD1

<400> SEQUENCE: 6

| | | | | | |
|---|---|---|---|---|---|
| atgctgtggt | gggaggaagt | ggaggactgc | tacgagagag | aggacgtgca | gaagaaaacc | 60 |
| ttcaccaagt | ggatcaacgc | ccagttcagc | aagttcggca | agcagcacat | cgagaacctg | 120 |
| ttcagcgatc | tgcaggatgg | caggagactg | ctggatctgc | tggagggact | gaccggccag | 180 |
| aagctgccca | aggagaaggg | cagcaccaga | gtgcacgccc | tgaacaacgt | gaacaaggcc | 240 |
| ctgagagtgc | tgcagaagaa | caacgtggac | ctggtggata | tcggcagcac | cgacatcgtg | 300 |
| gacggcaacc | acaagctgac | cctgggcctg | atctggaaca | tcatcctgca | ctggcaggtg | 360 |
| aagaacgtga | tgaagaacat | catggccggc | ctgcagcaga | ccaacagcga | agatcctg | 420 |
| ctgagctggg | tgaggcagag | caccagaaac | taccccagg | tgaacgtgat | caacttcacc | 480 |
| acctcctgga | gcgacggcct | ggccctgaac | gccctgatcc | acagccacag | acccgacctg | 540 |
| ttcgactgga | acagcgtggt | gtgtcagcag | agcgccaccc | agagactgga | gcacgccttc | 600 |
| aacatcgcca | gtaccagct | gggcatcgag | aagctgctgg | accccgagga | cgtggccacc | 660 |
| acctaccccg | acaagaaaag | catcctgatg | tatattacca | gcctgttcca | ggtgctgccc | 720 |
| cagcaggtgt | ccatcgaggc | catccaggaa | gtggaaatgc | tgcccaggcc | cagcaaagtg | 780 |
| accagggagg | agcacttcca | gctgcaccac | cagatgcact | atagccagca | gatcaccgtg | 840 |
| tccctggccc | agggctatga | gagagcccct | agcagcccca | agcccggtt | caagagctac | 900 |
| gcctacaccc | aggccgccta | cgtgaccacc | tccgacccca | ccagaagccc | cctgcccagc | 960 |
| cagcacctgg | agacccctga | ggataagagc | ttcggcagaa | gcctgaccga | gaccgaggcc | 1020 |
| aacctggata | gctaccagac | cgccctggag | gaagtgctgt | cttggctgct | gtccgccgag | 1080 |
| gacgccctgc | aggcccaggg | cgagatcagc | aacgacgtgg | aagaagtgaa | ggagcagttc | 1140 |
| cacacccacg | agggctacat | gatggacctg | accagccacc | agggcagagt | gggcaacgtg | 1200 |
| ctgcagctgg | gcagccagct | gatcggcacc | ggcaagctga | gcgaggacga | ggagaccgaa | 1260 |
| gtgcaggaac | agatgaacct | gctgaacagc | agatgggagt | gcctgagagt | ggccagcatg | 1320 |
| gagaagcaga | gcaacctgca | caaagtgctg | atggatctgc | agaaccagca | gctgaaggag | 1380 |
| ctgaacgact | ggctgaccaa | gacagaggag | cggacccgga | agatggagaa | ggagcccctg | 1440 |
| ggccctgaca | tcgaggacct | gaagaggcag | gtgcagcagc | ataaggtcct | gcaggaggat | 1500 |
| ctggagcagg | gcaggtgcg | cgtgaacagc | ctgacccaca | tggtggtcgt | ggtggacgag | 1560 |
| agcagcggcg | accacgccac | agccgccctg | aagagcagc | tgaaagtgct | gggcggcaga | 1620 |
| tgggccaata | tctgccggtg | gaccgaggac | agatgggtgc | tgctgcagga | catcctgctg | 1680 |
| aagtggcaga | gattcaccga | ggagcagtgc | ctgtttagcg | cctggctgag | cgagaaggag | 1740 |
| gacgccgtga | acaagatcca | caccaccggc | ttcaaggacc | agagcgaagt | gctgtccaac | 1800 |
| ctgcagaagc | tggccgtgct | gaaaaccgac | ctggagaaga | aaagcagac | catggacaag | 1860 |
| ctgtgcagcc | tgaaccagga | cctgctgagc | gccctgaaga | caccgtggt | ggcccacaag | 1920 |
| atggaggcct | ggctggataa | tagcgctcag | agatgggata | tctggtgca | gaaactggag | 1980 |
| aagagcagcg | cccagatcag | ccaggccgtg | accaccaccc | agcccagcct | gacacagacc | 2040 |
| accgtgatgg | agaccgtgac | catggtgacc | accagggagc | acatcctggt | gaagcacgcc | 2100 |
| caggaggagc | tgcccctcc | ccccctcag | aagaagcggc | agatcatcgt | ggatgccctg | 2160 |
| gagagactgc | aggagctgca | ggaagccacc | gacgagctgg | acctgaagct | gagacaggcc | 2220 |

-continued

```
gaagtgatca agggcagctg gcagcctgtg ggcgatctgc tgatcgacag cctgcaggac    2280
cacctggaga aagtgaaggc cctgcggggc gagaccaccc ccctgaagga aacgtgtcc     2340 tacgtgaacg acctggccag acagctgacc accctgggca ttcagctgag cccctacaac    2400
ctgaacaccc tggaggatct gaacacccgg tggaaactgc tgcaggtggc cattgaggac    2460
cggatcaggc agctgcacga ggcccacaga gacttcggcc ctgcttctca gcatttcctg    2520
agcaccagcg tgcagggccc ctgggagaga gccatcagcc caacaaagt gccctactac     2580 atcaaccacg agacccagac cacctgctgg gaccacccta agatgaccga gctgtaccag    2640
agcctggccg acctgaacaa tgtgcggttc agcgcctaca gaaccgccat gaagctgcgg    2700
agactgcaga aggccctgtg cctggacctg ctgtccctga gcgccgcctg cgacgccctg    2760
gaccagcaca acctgaagca gaacgaccag cccatggata tcctgcaggt gatcaactgc    2820
ctgaccacca tctacgatcg gctggagcag gagcacaaca acctggtgaa cgtgcccctg    2880
tgcgtggaca tgtgcctgaa ttggctgctg aacgtgtacg acaccggcag gaccggcaga    2940
atcagagtgc tgtccttcaa gaccggcatc atcagcctgt gcaaggccca cctggaggat    3000
aagtaccgct acctgttcaa gcaggtggcc agcagcaccg gcttctgcga tcagaggaga    3060
ctgggcctgc tgctgcacga tagcatccag atccctaggc agctgggcga agtggccagc    3120
tttggcggca gcaacatcga gccctctgtg aggagctgct tccagttcgc caacaacaag    3180
cccgagatcg aggccgccct gttcctggat tggatgaggc tggagcccca gagcatggtg    3240
tggctgcctg tgctgcacag agtggccgcc gccgagaccg ccaagcacca ggccaagtgc    3300
aacatctgca aggagtgccc catcatcggc ttccggtaca ggagcctgaa gcacttcaac    3360
tacgacatct gccagagctg ctttttcagc ggcagagtgg ccaagggcca caagatgcac    3420
taccccatgg tggagtactg cacccccacc acctccggcg aggatgtgag agacttcgcc    3480
aaagtgctga gaataagtt ccggaccaag cggtactttg ccaagcaccc caggatgggc    3540
tacctgcccg tgcagaccgt gctggagggc gacaacatgg agaccgacac catgtgatga    3600
tga                                                                  3603
```

<210> SEQ ID NO 7
<211> LENGTH: 1199
<212> TYPE: PRT
<213> ORGANISM: Artificial Sequence
<220> FEATURE:
<223> OTHER INFORMATION: murine MD1

<400> SEQUENCE: 7

```
Met Leu Trp Trp Glu Glu Val Glu Asp Cys Tyr Glu Arg Glu Asp Val
1               5                   10                  15

Gln Lys Lys Thr Phe Thr Lys Trp Ile Asn Ala Gln Phe Ser Lys Phe
            20                  25                  30

Gly Lys Gln His Ile Asp Asn Leu Phe Ser Asp Leu Gln Asp Gly Lys
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Lys Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110
```

-continued

```
Asn Ile Ile Leu His Trp Gln Val Lys Asn Val Met Lys Thr Ile Met
            115                 120                 125

Ala Gly Leu Gln Gln Thr Asn Ser Glu Lys Ile Leu Leu Ser Trp Val
130                 135                 140

Arg Gln Ser Thr Arg Asn Tyr Pro Gln Val Asn Val Ile Asn Phe Thr
145                 150                 155                 160

Ser Ser Trp Ser Asp Gly Leu Ala Leu Asn Ala Leu Ile His Ser His
                165                 170                 175

Arg Pro Asp Leu Phe Asp Trp Asn Ser Val Val Ser Gln His Ser Ala
                180                 185                 190

Thr Gln Arg Leu Glu His Ala Phe Asn Ile Ala Lys Cys Gln Leu Gly
            195                 200                 205

Ile Glu Lys Leu Leu Asp Pro Glu Asp Val Ala Thr Thr Tyr Pro Asp
210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Met Leu Pro Arg
                245                 250                 255

Thr Ser Ser Lys Val Thr Arg Glu Glu His Phe Gln Leu His His Gln
            260                 265                 270

Met His Tyr Ser Gln Gln Ile Thr Val Ser Leu Ala Gln Gly Tyr Glu
        275                 280                 285

Gln Thr Ser Ser Ser Pro Lys Pro Arg Phe Lys Ser Tyr Ala Phe Thr
    290                 295                 300

Gln Ala Ala Tyr Val Ala Thr Ser Asp Ser Thr Gln Ser Pro Tyr Pro
305                 310                 315                 320

Ser Gln His Leu Glu Ala Pro Arg Asp Lys Ser Leu Asp Ser Ser Leu
                325                 330                 335

Met Glu Thr Glu Val Asn Leu Asp Ser Tyr Gln Thr Ala Leu Glu Glu
            340                 345                 350

Val Leu Ser Trp Leu Leu Ser Ala Glu Asp Thr Leu Arg Ala Gln Gly
        355                 360                 365

Glu Ile Ser Asn Asp Val Glu Val Lys Glu Gln Phe His Ala His
    370                 375                 380

Glu Gly Phe Met Met Asp Leu Thr Ser His Gln Gly Leu Val Gly Asn
385                 390                 395                 400

Val Leu Gln Leu Gly Ser Gln Leu Val Gly Lys Gly Lys Leu Ser Glu
                405                 410                 415

Asp Glu Glu Ala Glu Val Gln Glu Gln Met Asn Leu Leu Asn Ser Arg
            420                 425                 430

Trp Glu Cys Leu Arg Val Ala Ser Met Glu Lys Gln Ser Lys Leu His
        435                 440                 445

Lys Val Leu Met Asp Leu Gln Asn Gln Lys Leu Lys Glu Leu Asp Asp
450                 455                 460

Trp Leu Thr Lys Thr Glu Glu Arg Thr Lys Lys Met Glu Glu Glu Pro
465                 470                 475                 480

Phe Gly Pro Asp Leu Glu Asp Leu Lys Cys Gln Val Gln Gln His Lys
                485                 490                 495

Val Leu Gln Glu Asp Leu Glu Gln Glu Gln Val Arg Val Asn Ser Leu
            500                 505                 510

Thr His Met Val Val Val Asp Glu Ser Ser Gly Asp His Ala Thr
        515                 520                 525
```

```
Ala Ala Leu Glu Glu Gln Leu Lys Val Leu Gly Asp Arg Trp Ala Asn
        530                 535                 540
Ile Cys Arg Trp Thr Glu Asp Arg Trp Ile Val Leu Gln Asp Ile Leu
545                 550                 555                 560
Leu Lys Trp Gln His Phe Thr Glu Gln Cys Leu Phe Ser Thr Trp
                565                 570                 575
Leu Ser Glu Lys Glu Asp Ala Met Lys Asn Ile Gln Thr Ser Gly Phe
                580                 585                 590
Lys Asp Gln Asn Glu Met Met Ser Ser Leu His Lys Ile Ser Thr Leu
        595                 600                 605
Lys Ile Asp Leu Glu Lys Lys Pro Thr Met Glu Lys Leu Ser Ser
    610                 615                 620
Leu Asn Gln Asp Leu Leu Ser Ala Leu Lys Asn Lys Ser Val Thr Gln
625                 630                 635                 640
Lys Met Glu Ile Trp Met Glu Asn Phe Ala Gln Arg Trp Asp Asn Leu
                645                 650                 655
Thr Gln Lys Leu Glu Lys Ser Ser Ala Gln Ile Ser Gln Ala Val Thr
                660                 665                 670
Thr Thr Gln Pro Ser Leu Thr Gln Thr Thr Val Met Glu Thr Val Thr
        675                 680                 685
Met Val Thr Thr Arg Glu Gln Ile Met Val Lys His Ala Gln Glu Glu
        690                 695                 700
Leu Pro Pro Pro Pro Gln Lys Lys Arg Gln Ile Thr Val Asp Ala
705                 710                 715                 720
Leu Glu Arg Leu Gln Glu Leu Gln Glu Ala Asp Glu Leu Asp Leu
                725                 730                 735
Lys Leu Arg Gln Ala Glu Val Ile Lys Gly Ser Trp Gln Pro Val Gly
        740                 745                 750
Asp Leu Leu Ile Asp Ser Leu Gln Asp His Leu Glu Lys Val Lys Ala
        755                 760                 765
Leu Arg Gly Glu Ile Ala Pro Leu Lys Glu Asn Val Asn Arg Val Asn
    770                 775                 780
Asp Leu Ala His Gln Leu Thr Thr Leu Gly Ile Gln Leu Ser Pro Tyr
785                 790                 795                 800
Asn Leu Ser Thr Leu Glu Asp Leu Asn Thr Arg Trp Arg Leu Leu Gln
                805                 810                 815
Val Ala Val Glu Asp Arg Val Arg Gln Leu His Glu Ala His Arg Asp
                820                 825                 830
Phe Gly Pro Ala Ser Gln His Phe Leu Ser Thr Ser Val Gln Gly Pro
        835                 840                 845
Trp Glu Arg Ala Ile Ser Pro Asn Lys Val Pro Tyr Tyr Ile Asn His
850                 855                 860
Glu Thr Gln Thr Thr Cys Trp Asp His Pro Lys Met Thr Glu Leu Tyr
865                 870                 875                 880
Gln Ser Leu Ala Asp Leu Asn Asn Val Arg Phe Ser Ala Tyr Arg Thr
                885                 890                 895
Ala Met Lys Leu Arg Arg Leu Gln Lys Ala Leu Cys Leu Asp Leu Leu
                900                 905                 910
Ser Leu Ser Ala Ala Cys Asp Ala Leu Asp Gln His Asn Leu Lys Gln
        915                 920                 925
Asn Asp Gln Pro Met Asp Ile Leu Gln Ile Ile Asn Cys Leu Thr Thr
    930                 935                 940
Ile Tyr Asp Arg Leu Glu Gln Glu His Asn Asn Leu Val Asn Val Pro
```

```
                       945                  950                  955                  960
        Leu Cys Val Asp Met Cys Leu Asn Trp Leu Leu Asn Val Tyr Asp Thr
                        965                  970                  975
        Gly Arg Thr Gly Arg Ile Arg Val Leu Ser Phe Lys Thr Gly Ile Ile
                        980                  985                  990
        Ser Leu Cys Lys Ala His Leu Glu Asp Lys Tyr Arg Tyr Leu Phe Lys
                        995                 1000                 1005
        Gln Val Ala Ser Ser Thr Gly Phe Cys Asp Gln Arg Arg Leu Gly Leu
                       1010                 1015                 1020
        Leu Leu His Asp Ser Ile Gln Ile Pro Arg Gln Leu Gly Glu Val Ala
        1025                 1030                 1035                 1040
        Ser Phe Gly Gly Ser Asn Ile Glu Pro Ser Val Arg Ser Cys Phe Gln
                       1045                 1050                 1055
        Phe Ala Asn Asn Lys Pro Glu Ile Glu Ala Ala Leu Phe Leu Asp Trp
                       1060                 1065                 1070
        Met Arg Leu Glu Pro Gln Ser Met Val Trp Leu Pro Val Leu His Arg
                       1075                 1080                 1085
        Val Ala Ala Ala Glu Thr Ala Lys His Gln Ala Lys Cys Asn Ile Cys
        1090                 1095                 1100
        Lys Glu Cys Pro Ile Ile Gly Phe Arg Tyr Arg Ser Leu Lys His Phe
        1105                 1110                 1115                 1120
        Asn Tyr Asp Ile Cys Gln Ser Cys Phe Phe Ser Gly Arg Val Ala Lys
                       1125                 1130                 1135
        Gly His Lys Met His Tyr Pro Met Val Glu Tyr Cys Thr Pro Thr Thr
                       1140                 1145                 1150
        Ser Gly Glu Asp Val Arg Asp Phe Ala Lys Val Leu Lys Asn Lys Phe
                       1155                 1160                 1165
        Arg Thr Lys Arg Tyr Phe Ala Lys His Pro Arg Met Gly Tyr Leu Pro
                       1170                 1175                 1180
        Val Gln Thr Val Leu Glu Gly Asp Asn Met Glu Thr Asp Thr Met
        1185                 1190                 1195

<210> SEQ ID NO 8
        <211> LENGTH: 3611
        <212> TYPE: DNA
        <213> ORGANISM: Artificial Sequence
        <220> FEATURE:
        <223> OTHER INFORMATION: opt murine MD1

<400> SEQUENCE: 8
atgctgtggt gggaggaagt ggaggactgc tacgagagag aggacgtgca gaagaaaacc         60
ttcaccaagt ggatcaacgc ccagttcagc aagttcggca gcagcacat cgacaacctg        120 ttcagcgacc tgcaggacgg caagagactg ctggatctgc tggagggact gaccggccag        180
aagctgccca aggagaaggg cagcaccaga gtgcacgccc tgaacaacgt gaacaaggcc        240
ctgagagtgc tgcagaagaa caacgtggac ctggtgaata tcggcagcac cgacatcgtg        300
gacggcaacc acaagctgac cctgggcctg atctggaaca tcatcctgca ctggcaggtg        360
aagaacgtga tgaaaaccat catggccggc ctgcagcaga ccaacagcga agatcctg        420 ctgagctggg tgaggcagag caccagaaac taccccagg tgaacgtgat caacttcacc        480
agcagctgga gcgacggcct ggccctgaac gccctgatcc acagccacag acccgacctg        540
ttcgactgga cagcgtggt gtcccagcac agcgccaccc agagactgga gcacgccttc        600
aacatcgcca gtgccagct gggcatcgag aagctgctgg accccgagga cgtggccacc        660
```

```
acctaccccg acaagaaaag catcctcatg tatatcacct ctctgtttca ggtgctgccc      720
cagcaggtgt ccatcgaggc catccaggaa gtggaaatgc tgccccggac cagcagcaaa      780
gtgacccggg aggagcactt ccagctgcac caccagatgc actatagcca gcagatcacc      840
gtgtccctgg cccagggcta cgagcagacc agcagctccc ccaagcccag attcaagagc      900
tacgccttca cccaggccgc ctacgtggcc acaagcgata gcacccagag cccctacccc      960
agccagcacc tggaggcccc tagagacaag agcctggaca gcagcctgat ggagacagaa     1020
gtgaacctgg acagctacca gaccgccctg aggaagtgc tgtcttggct gctgtccgcc     1080
gaggacaccc tgagagccca gggcgagatc agcaacgacg tggaagaagt gaaggagcag     1140
ttccacgccc acgagggctt catgatggac ctgacctccc atcagggcct ggtgggcaac     1200
gtgctgcagc tggcagcca gctcgtggga agggcaagc tgagcgagga cgaggaggcc     1260
gaagtgcagg aacagatgaa cctgctgaac agcagatggg agtgcctgag agtggccagc     1320
atggagaagc agagcaagct gcacaaagtg ctgatggatc tgcagaacca gaagctgaag     1380
gaactggacg actggctgac caagaccgag gagcggacca agaagatgga ggaggagccc     1440
ttcggccccg acctggagga cctgaagtgc caggtgcagc agcataaggt cctgcaggag     1500
gacctggaac aggagcaggt gcgcgtgaac agcctgaccc acatggtggt cgtggtggac     1560
gagagcagcg gcgaccacgc cacagccgcc ctggaagagc agctgaaagt gctgggcgac     1620
agatgggcca atatctgccg gtggaccgag gatagatgga tcgtgctgca ggacatcctg     1680
ctgaagtggc agcacttcac cgaggagcag tgcctgtttta gcacctggct gagcgagaaa     1740
gaggacgcca tgaagaacat ccagaccagc ggcttcaagg accagaacga gatgatgagc     1800
agcctgcaca agatcagcac cctgaagatc gacctggaga agaaaaagcc cacaatggag     1860
aagctgtcca gcctgaacca ggacctgctg agcgccctga agaacaagag cgtgacccag     1920
aaaatggaga tctggatgga gaatttcgca cagaggtggg acaacctgac ccagaagctg     1980
gagaagagca gcgcccagat cagccaggcc gtgaccacca cccagcccag cctgacacag     2040
accaccgtga tggagaccgt gaccatggtg accacccggg agcagatcat ggtgaagcac     2100
gcccaggagg agctgccccc tcccccccct cagaagaagc ggcagatcac agtggatgcc     2160
ctggagagac tgcaggagct gcaggaagcc gccgacgagc tggatctgaa gctgagacag     2220
gccgaagtga tcaagggcag ctggcagcct gtggcgatc tgctgatcga cagcctgcag     2280
gaccacctgg agaaagtgaa ggccctgcgg ggcgagatcg ccccctgaa ggagaacgtg     2340
aaccgcgtga cgacctggc ccatcagctg accaccctgg gcattcagct gagcccctac     2400
aacctgagca ccctggagga tctgaacacc cggtggagac tgctgcaggt ggccgtggag     2460
gatagagtga ggcagctgca cgaggcccac agagacttcg ccctgcctc ccagcacttc     2520
ctgagcacca gcgtgcaggg cccctgggag agagccatca gccccaacaa agtgccctac     2580
tacatcaacc acgagaccca gaccacctgc tgggaccacc ctaagatgac cgagctgtac     2640
cagagcctgg ccgacctgaa caatgtgcgg ttcagcgcct acagaaccgc catgaagctg     2700
cggagactgc agaaggccct gtgcctggac ctgctgtccc tgagcgccgc ctgcgacgcc     2760
ctggaccagc acaacctgaa gcagaacgac cagcccatgg atatcctgca gatcatcaac     2820
tgcctgacca ccatctacga tcggctggag caggagcaca caacctggt gaacgtgccc     2880
ctgtgcgtgg acatgtgcct gaattggctg ctgaacgtgt acgacaccgg caggaccggc     2940
agaatcagag tgctgtcctt caagaccggc atcatcagcc tgtgcaaggc ccacctggag     3000
gataagtacc gctacctgtt caagcaggtg gccagcagca ccggcttctg cgatcagagg     3060
```

```
                                                        -continued agactgggcc tgctgctgca cgatagcatc cagatcccta ggcagctggg cgaagtggcc    3120
agctttggcg gcagcaacat cgagccctct gtgaggagct gcttccagtt cgccaacaac    3180
aagcccgaga tcgaggccgc cctgttcctg gattggatga ggctggagcc ccagagcatg    3240
gtgtggctgc ctgtgctgca cagagtggcc gccgccgaga ccgccaagca ccaggccaag    3300
tgcaacatct gcaaggagtg ccccatcatc ggcttccggt acaggagcct gaagcacttc    3360
aactacgaca tctgccagag ctgcttttc agcggcagag tggccaaggg ccacaagatg     3420
cactacccca tggtggagta ctgcaccccc accacctccg gcgaggatgt gagagacttc    3480
gccaaagtgc tgaagaataa gttccggacc aagcggtact ttgccaagca ccccaggatg    3540
ggctacctgc ccgtgcagac cgtgctggag ggcgacaaca tggagaccga caccatgtga    3600
tgtgatgatg a                                                         3611
```

EFFICIENT SYSTEMIC TREATMENT OF DYSTROPHIC MUSCLE PATHOLOGIES

CROSS REFERENCE TO RELATED APPLICATIONS

The present application is a continuation application of U.S. application Ser. No. 16/185,248 filed Nov. 9, 2018, now U.S. Pat. No. 10,786,546, which is a continuation application of U.S. Applicant Ser. No. 15/321,416 filed Dec. 22, 2016, now U.S. Pat. No. 10,166,272, which is a U.S. national phase application of PCT/EP2015/058964 filed Apr. 24, 2015, which claims priority to EP Application No. 14174848.3 filed Jun. 27, 2014. U.S. application Ser. Nos. 16/185,248 and 15/321,416 are herein incorporated by reference in their entity.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 390106-404C2-SEQUENCE_LISTING.txt. The text file is 56 KB, was created on Aug. 13, 2020, and is being submitted electronically via EFS-Web.

The present invention provides an efficient gene therapy product for dystrophic diseases, especially in humans and dogs, defined by the sequence encoding the microdystrophin, the delivery vehicle and the route of administration to be used.

BACKGROUND OF THE INVENTION

Duchenne muscular dystrophy (DMD) is the most frequent progressive muscle degenerative disease, affecting approximately one in 3,500 to 5,000 male births. DMD is caused by deletions or mutations in the gene encoding dystrophin, located on the X chromosome. Dystrophin is required for the assembly of the dystrophin-glycoprotein complex, and provides a mechanical and functional link between the cytoskeleton of the muscle fiber and the extracellular matrix. The absence of functional dystrophin causes fiber degeneration, inflammation, necrosis and replacement of muscle with scar and fat tissue, resulting in progressive muscle weakness and premature death due to respiratory and cardiac failure between the second and fourth decade of life (Moser, H., Hum Genet, 1984. 66(1): p. 17-40).

A milder form of the disease called Becker muscular dystrophy (BMD) is distinguished from DMD by delayed onset, later dependence on wheelchair support, and longer life span. BMD is caused by mutations maintaining the reading frame and the most critical parts of the gene, leading to a truncated but still functional dystrophin protein (Muntoni F et al, Lancet Neurol, 2003).

There is no cure nor effective treatment available for DMD (Rodino-Klapac, L. R. et al., Curr Neurol Neurosci Rep, 2013. 13(3): p. 332) or BMD. Conventional therapies are limited to supportive care, which partially alleviates signs and symptoms, but does not directly target the disease mechanism nor reverse the phenotype.

There currently are several therapeutic strategies being developed for DMD including in vivo gene therapy, cell transplantation therapy, pharmacologic rescue of DMD nonsense mutations and exon skipping strategies to repair the DMD gene reading frame. All of these strategies have problems to overcome, including targeting different muscle groups, optimization of delivery, long-term expression of the transgene, and potential immune response (Jamin et al., Expert Opin Biol Ther, 2014).

The dystrophin gene is the largest known gene in the human genome and is too large to fit inside known gene therapy vector systems. Therefore, as of today, there are essentially two gene therapy strategies for DMD with viral vectors: i) constitutive expression of antisense oligonucleotides to promote exon skipping, which is amenable to certain mutations only, and (ii) constitutive expression of a cDNA coding for a functional, reduced-size dystrophin protein ("microdystrophin" also known as "minidystrophin").

Both strategies, use of small antisense sequences or use of microdystrophin, address the major hurdle for the use of AAV vectors in DMD gene therapy, which is their packaging capacity. AAV vectors can accommodate about 4.7 kb while the size of the wild type dystrophin cDNA is about 14 kb. To overcome this issue, a number of studies have developed partially deleted but highly functional dystrophin genes, which can be successfully packaged inside AAV vectors and were shown to improve, though not completely normalize, the dystrophic phenotype in animal models.

The mdx mouse model is commonly used to test new constructs encoding microdystrophins. However, this model has drawbacks because the mdx mouse displays a less severe form of the disease, without immune reactions. The other animal model is the GRMD dog, which is considered more reliable to predict the therapeutic potential of a gene therapy product in humans (Kornegay et al., Mamm Genome, 2012).

Among all the proposed microdystrophin sequences, Foster H. et al. (Mol Ther, 2008. 16(11): p. 1825-32) compared in mice two different configurations of microdystrophin genes, $\Delta AB/R3$-R18/$\Delta CT$ and $\Delta R4$-R23/$\Delta CT$, under the control of a muscle-specific promoter (Spc5-12) in a recombinant AAV vector (rAAV2/8). It was reported that codon human optimization of microdystrophin improved gene transfer and muscle functions in the mdx mouse model. Intravenous injection of $3.10^{11}$ vg total of rAAV/8 allowed efficient cardiac gene transfer and marked dystrophin expression in the skeletal muscle and within the diaphragm.

In relation with CXMDj dogs, Ohshima S. et al. (Mol Ther, 2009. 17(1): p. 73-80) reported the administration into dogs of a rAAV8 encoding a M3 microdystrophin under the control of the CMV promoter by limb perfusion, i.e. intravenous injection under pressure.

Zhang Y. et al. (Hum Mol Genet, 2013. 22(18): p. 3720-29) studied the systemic ($5.10^{12}$ vg total) dual AAV9 gene therapy in DMD mice. By homologous recombination, the dual AAV vectors injected via the tail vain reconstituted a nNOS binding microdystrophin containing dystrophin repeats R16 and R17.

Similarly, Odom G. et al. (Mol Ther, 2011. 19(1): p. 36-45) demonstrated reconstitution of an expression cassette encoding a $\Delta H2$-R19 minidystrophin in mice following intravascular co-delivery of two rAAV6 vectors ($2.10^{12}$ vg total) sharing a central homologous recombinogenic region.

Wang B. et al. (J Orthop Res. 2009; 27(4): p 421-6) disclosed the intraperitoneal (i.p.) injection of $3.10^{11}$vg total rAAV1 vectors in neonatal mice (dKO and mdx). These AAV vectors encode the microdystrophin $\Delta 3990$ placed under the control of the MCK or CMV promoter.

Koppanati et al. (Gene therapy. 2010; 17(11): p 1355-62) reported in utero gene transfer in the mdx mouse via the intraperitoneal (i.p.) injection of $6.4.10^{11}$vg total rAAV8 vector encoding a canine microdystrophin placed under the control of the CMV promoter.

Schinkel et al. (Human Gene therapy. 2012; 23(6): p 566-75) reported cardiac gene therapy in the mdx mouse via the intravenous (IV) injection of $10^{12}$vg total rAAV9 vector encoding a microdystrophin placed under the control of the CMV promoter or the cardiac-specific MLC0.26 promoter.

Gregorevic et al. (Mol. Therapy 2008; 16(4): p 657-64) reported muscular gene therapy in the mdx mouse via the intravenous (IV) injection of $10^{13}$vg total rAAV6 vector encoding the ΔR4-R23/ΔCT microdystrophin placed under the control of the CMV promoter.

Shin et al. (Gene Therapy 2011; 18(9): p 910-19) reported cardiac gene therapy in the mdx mouse via the intravenous (IV) injection of $3.10^{12}$vg total rAAV9 vector encoding a microdystrophin (hΔCS2) placed under the control of the CMV promoter.

Shin et al. (J. of Gene Medicine 2008; 10(4): p 449) compared the delivery efficiency in mice of rAAV8 encoding the ΔCS2 microdystrophin placed under the control of the CMV promoter, by subcutaneous injection or intravenous injection.

Colgan et al. (Mol. Therapy 2014; 22(S1): p S197) reported the microdystrophin and follistatin combinatorial gene delivery by intravenous injection of rAAV6 vectors in dKO mice.

In the context of DMD, a valuable therapeutic solution would be a gene therapy product having the following characteristics:
  A product which can be systemically administered, at a reasonable dose (i.e. a proper gene transfer in the target tissues) and possibly by a unique injection;
  A product which is has acceptable toxicity at that dose, and especially does not induce an adverse immune response against the dystrophin protein;
  A product having a satisfying tropism, i.e. a wide spread gene transfer on large territories of skeletal muscles, but also diaphragm and myocardium;
  A product able to ameliorate the dystrophic disease in humans.

In practice, previous reports have revealed that it is a very challenging task and several attempts have failed:

Studies using AAV2/6 vectors encoding a human-specific, but not codon-optimized, microdystrophin (ΔR4-R23/ΔCT) under a CMV promoter resulted in the limited expression and eventual destruction of injected CXMDj dog muscle fibers via the immune system at 6 weeks after discontinuation of immunosuppression, 22 weeks after initial intramuscular injection (Wang, Z. et al., Mol Ther, 2007. 15: p. 1160-66).

Clinical trials based on the intramuscular injection of AAV2/5 vectors encoding a human-specific, but not codon-optimized, microdystrophin (ΔR4-R21/ΔCT) under a CMV promoter resulted in very limited transgene expression and in an inappropriate immune response (Mendell, J R et al., N Engl J Med, 2010.363(15): p. 1429-37; Bowles, D E. et al., Mol Ther, 2012. 20(2): p. 443-55).

Therefore, there is a need in the art for an efficient treatment of dystrophic pathologies in humans, including systemic benefits in terms of survival, overall clinical score, cardiac and/or respiratory function.

BRIEF SUMMARY OF THE INVENTION

The present invention aims at alleviating or curing the devastating Duchenne muscular dystrophy (DMD) by expressing a shorter but functional dystrophin polypeptide called microdystrophin.

For the first time, the present invention offers a promising gene therapy product, a sequence optimized microdystrophin, encapsidated in the AAV8 capsid, for treating dystrophic diseases. After systemic intravenous administration of a single dose, not only is the microdystrophin highly expressed in multiple muscles but it also results in muscle pathology improvement and improved clinical outcome measures.

Indeed, so good results obtained in a dog model, in terms of muscular, respiratory and cardiac rescue, correlated with a prolonged life in good condition, have never been reported so far in relation with this kind of pathology.

Definitions

The articles "a" and "an" are used herein to refer to one or to more than one (i.e., to at least one) of the grammatical object of the article. By way of example, "an element" means one element or more than one element.

"About" or "approximately" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA or a cDNA may also include introns to the extent that the nucleotide sequence encoding the protein may in some version contain an intron(s).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Identical" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous or identical at that position. The percent of homology/identity between two sequences is a function of the number of matching positions shared by the two sequences divided by the number of positions compared X 100. For example, if 6 of 10 of the positions in two sequences are matched then the two sequences are 60% identical. Generally, a comparison is made when two sequences are aligned to give maximum homology/identity.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence, which is required for expression of a gene product operably linked to the promoter/regulatory sequence. In some instances, this sequence may be the core promoter sequence and in other instances, this sequence may also include an enhancer sequence and other regulatory elements, which are required for expression of the gene product. The promoter/regulatory sequence may, for example, be one, which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell preferentially if the cell is a cell of the tissue type corresponding to the promoter.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics, which are normal or expected for one cell or tissue type, might be abnormal for a different cell or tissue type.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" or "ameliorated" if the severity of a symptom of the disease or disorder, the frequency with which such a symptom is experienced by a patient, or both, is reduced. This also includes halting progression of the disease or disorder. A disease or disorder is "cured" if the severity of a symptom of the disease or disorder, the frequency with which such a symptom is experienced by a patient, or both, is eliminated.

A "therapeutic" treatment is a treatment administered to a subject who exhibits signs of pathology, for the purpose of diminishing or eliminating those signs.

As used herein, "treating a disease or disorder" means reducing the frequency or severity of at least one sign or symptom of a disease or disorder experienced by a subject. Disease and disorder are used interchangeably herein in the context of treatment.

An "effective amount" of a compound is that amount of compound which is sufficient to provide a beneficial effect to the subject to which the compound is administered. The phrase "therapeutically effective amount", as used herein, refers to an amount that is sufficient or effective to prevent or treat (delay or prevent the onset of, prevent the progression of, inhibit, decrease or reverse) a disease or condition, including alleviating symptoms of such diseases. An "effective amount" of a delivery vehicle is that amount sufficient to effectively bind or deliver a compound.

DETAILED DESCRIPTION OF THE INVENTION

In one embodiment, the present invention relates to a composition comprising a gene therapy product for use in the treatment of a dystrophic disease in a subject, wherein:
the gene therapy product comprises a nucleic acid sequence encoding a functional microdystrophin;
the composition is systemically administered.

In other words, the present invention provides a method for treating a dystrophic disease in a subject, comprising systemically administrating to the subject a composition comprising a nucleic acid sequence encoding a functional microdystrophin.

In one embodiment, the present invention provides a method for treating a dystrophic disease in a subject, comprising systemically administrating to the subject a gene therapy product comprising a nucleic acid sequence encoding a functional microdystrophin. The invention concerns the use of a gene therapy product comprising a nucleic acid sequence encoding a functional microdystrophin for the preparation of a medicament for the treatment of dystrophic diseases, wherein the medicament is systemically administered.

According to a first aspect, the present invention relates to a gene therapy product for use in the treatment of a dystrophic disease in a subject.

Typically, a gene therapy product is made of 2 components:
The encapsidated recombinant nucleic acid sequence which defines the expression cassette that provides the therapeutic benefit(s) once expressed in the target cell/tissue; and
The viral capsid which allows proper gene transfer and to a certain extent, tissue tropism.

According to one aspect, the gene therapy product comprises a nucleic acid sequence encoding a functional microdystrophin.

In the frame of the invention, microdystrophin means a peptide or protein, which is shorter than the native or wild type dystrophin. In the context of the invention, the terms "microdystrophin" and "minidystrophin" have the same meaning. In the rest of the application, the term "microdystrophin" will be used, as well as the abbreviations "MD" or "μDys".

A "functional" microdystrophin means that the corresponding peptide or protein is able to perform at least some of the functions of the wild-type dystrophin protein and is able to alleviate, at least partially, one or more of the symptoms associated with the absence of a native dystrophin, especially fiber degeneration, inflammation, necrosis, replacement of muscle with scar and fat tissue, muscle weakness, respiratory and cardiac failure, as well as premature death.

The structure of dystrophin is well documented (see FIG. 1) and active fragments thereof have been disclosed (Athanasopoulos et al., Gene Ther 2004 Suppl 1:S109-21). As would be understood in the art, an active fragment is a portion or portions of a full length sequence that retain the biological function of the full length sequence.

The full-length dystrophin is characterized by different domains:
A N-terminal domain which binds to actin;
4 hinge domains (H1 to H4);
24 spectrin-like repeats or rod domains (1 to 24);
A cysteine-rich domain;
A C-terminal domain.

According to one embodiment, the microdystrophin has at least one domain lacking, advantageously at least one spectrin-like-repeat.

According to a particular embodiment, the microdystrophin has the configuration ΔR4-R23/ΔCT, comprising 4 spectrin-like repeats, i.e. spectrin-like repeats 1, 2, 3 and 24 as shown on FIG. 1. More precisely, this sequence comprises deletions of rod domains 4-23 and exons 71-78 of the CT domain of dystrophin, and contains the last three amino acids of exon 79 of dystrophin followed by three stop codons.

Such a microdystrophin noted ΔR4-R23/ΔCT or MD1 has e.g. the amino acid sequence shown in SEQ ID NO: 3, 4 or 7.

In one embodiment, the nucleic acid sequence encoding the functional microdystrophin, also named ORF for "open reading frame", is a cDNA. However, e.g. single- or double-stranded DNA or RNA can be used.

In a specific embodiment, the present invention provides compositions comprising nucleic acid sequences that are shorter than the wild-type dystrophin cDNA.

When used in the context of AAV vectors, which can accommodate about 4.7 kb, the nucleic acid sequence encoding the functional microdystrophin, as well as all the sequences required for its proper expression, should not exceed this packaging capacity. In one embodiment, the nucleic acid sequence encoding the functional microdystrophin does not exceed 4500, 4000 bp, preferably 3900, 3800, 3700, 3600 or even 3500 bp.

The nucleic acid sequence encoding the functional microdystrophin is advantageously of human origin but can also be a non-human primate, a canine, a rat or a murine sequence. In one embodiment, the nucleic acid sequence originates from the organism it will be administered to (e.g. a human sequence in humans).

According to another embodiment, the nucleic acid sequence encoding said microdystrophin is optimized for use in a given subject, advantageously in humans. Preferably, this optimized sequence is modified as follows:

The sequence is modified to include a consensus Kozak sequence before AUG start codon within mRNA, to improve initiation of translation.

The sequence is optimized based on transfer RNA frequencies in human and GC content is increased to promote RNA stability. As a result and in a specific case, codon optimization for humans advantageously leads to 63% of codons being modified and the GC content increased to over 60%. This of course depends on the original (before optimization) microdystrophin sequence and the target host.

According to one embodiment, the nucleic acid sequence encoding a functional microdystrophin corresponds to:

nucleotides 586 to 4185 of sequence SEQ ID NO: 1 as shown in SEQ ID NO: 5; or nucleotides 586 to 4188 of sequence SEQ ID NO: 2 as shown in SEQ ID NO: 6.

According to one embodiment, said sequence can be an isolated nucleic acid encoding a microdystrophin having substantial homology or identity (60%, 70%, 80%, 90% 95% or even 99%) to the peptides disclosed herein, especially of sequence SEQ ID NO: 3, SEQ ID NO: 4, or even SEQ ID NO: 7.

Preferably, the nucleotide sequence of an isolated nucleic acid encoding a peptide of the invention is "substantially homologous/identical", that is, is about 60% homologous, more preferably about 70% homologous, even more preferably about 80% homologous, more preferably about 90% homologous, even more preferably, about 95% homologous, and even more preferably about 97%, 98% or even 99% homologous to a nucleotide sequence of an isolated nucleic acid encoding the functional microdystrophin, especially of sequence SEQ ID NO:5, SEQ ID NO: 6 or even SEQ ID NO: 8.

According to another aspect, the nucleotide sequence harbored by an expression vector according to the invention is "substantially homologous/identical", that is, is about 60% homologous, more preferably about 70% homologous, even more preferably about 80% homologous, even more preferably about 90% homologous, even more preferably about 95% homologous, and even more preferably about 97%, 98% or even 99% homologous to the sequence SEQ ID NO: 1 or SEQ ID NO: 2.

In another embodiment, the composition comprises a plasmid or a vector. According to a specific embodiment, the isolated nucleic acid is inserted into the vector. In brief summary, the expression of natural or synthetic nucleic acids is typically achieved by operably linking a nucleic acid or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

In one embodiment, the composition comprises an expression vector, advantageously a viral vector. Of particular interest are the expression vectors which packaging capacity does not allow accommodation of the (wild type) dystrophin gene, including the (wild type) dystrophin cDNA.

In one embodiment, the viral vector is selected from the group consisting of a baculoviral vector, herpes viral vector, lentiviral vector, retroviral vector, adenoviral vector, and adeno-associated viral (AAV) vector.

According to a specific embodiment of the invention, the viral vector containing the expression construct is an adeno-associated viral (AAV) vector.

Adeno-associated viral (AAV) vectors have become powerful gene delivery tools for the treatment of various disorders. AAV vectors possess a number of features that render them ideally suited for gene therapy, including a lack of pathogenicity, moderate immunogenicity, and the ability to transduce post-mitotic cells and tissues in a stable and efficient manner. Expression of a particular gene contained within an AAV vector can be specifically targeted to one or more types of cells by choosing the appropriate combination of AAV serotype, promoter, and delivery method.

In one embodiment, the encoding sequence is contained within an AAV vector. More than 100 naturally occurring serotypes of AAV are known. Many natural variants in the AAV capsid exist, allowing identification and use of an AAV with properties specifically suited for dystrophic pathologies. AAV viruses may be engineered using conventional molecular biology techniques, making it possible to optimize these particles for cell specific delivery of nucleic acid sequences, for minimizing immunogenicity, for tuning stability and particle lifetime, for efficient degradation, for accurate delivery to the nucleus.

As mentioned above, the use of AAV vectors is a common mode of exogenous delivery of DNA as it is relatively non-toxic, provides efficient gene transfer, and can be easily optimized for specific purposes. Among the serotypes of AAVs isolated from human or non-human primates (NHP) and well characterized, human serotype 2 is the first AAV that was developed as a gene transfer vector. Other currently used AAV serotypes include AAV1, AAV3, AAV4, AAV5, AAV6, AAV7, AAV8, AAV9, AAV10, AAV11 and AAV12. In addition, non-natural engineered variants and chimeric AAV can also be useful.

Desirable AAV fragments for assembly into vectors include the cap proteins, including the vp 1, vp2, vp3 and hypervariable regions, the rep proteins, including rep 78, rep 68, rep 52, and rep 40, and the sequences encoding these proteins. These fragments may be readily utilized in a variety of vector systems and host cells.

Such fragments may be used alone, in combination with other AAV serotype sequences or fragments, or in combination with elements from other AAV or non-AAV viral sequences. As used herein, artificial AAV serotypes include, without limitation, AAV with a non-naturally occurring capsid protein. Such an artificial capsid may be generated by any suitable technique, using a selected AAV sequence (e.g., a fragment of a vpl capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid. Thus exemplary AAVs, or artificial AAVs, include AAV2/8 (U.S. Pat. No. 7,282,199), AAV2/5 (available from the National Institutes of Health), AAV2/9 (WO2005/033321), AAV2/6 (U.S. Pat. No. 6,156,303), and AAVrh8 (WO2003/042397), among others. In one embodiment, the vectors useful in the compositions and methods described herein contain, at a minimum, sequences encoding a selected AAV serotype capsid, e.g., an AAV8 capsid, or a fragment thereof. In another embodiment, useful vectors contain, at a minimum, sequences encoding a selected AAV serotype rep protein, e.g., AAV8 rep protein, or a fragment thereof. Optionally, such vectors may contain both AAV cap and rep proteins. In vectors in which both AAV rep and cap are provided, the AAV rep and AAV cap sequences can both be of one serotype origin, e.g., all AAV8 origin. Alternatively, vectors may be used in which the rep sequences are from an AAV serotype, which differs from that which is providing the cap sequences. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector, such as AAV2/8 (U.S. Pat. No. 7,282,199).

According to one embodiment, the composition comprises an AAV of serotype 2, 5, 8 or 9. Advantageously, the claimed vector is an AAV8 or AAV9 vector, especially an AAV2/8 or AAV2/9 vector. More advantageously, the claimed vector is an AAV8 vector or an AAV2/8 vector.

In the AAV vectors used in the present invention, the AAV genome may be either a single stranded (ss) nucleic acid or a double stranded (ds)/self complementary (sc) nucleic acid molecule.

Advantageously, the nucleic acid sequence encoding the functional microdystrophin is inserted between the ITR («Inverted Terminal Repeat») sequences of the AAV vector. Typical ITR sequences correspond to:
  nucleotides 1 to 128 of sequence SEQ ID NO: 1 or of sequence SEQ ID NO: 2 (5'ITR sequences);
  nucleotides 4511 to 4640 of sequence SEQ ID NO: 1 or nucleotides 4514 to 4643 of sequence SEQ ID NO: 2 (3' ITR sequences).

Recombinant viral particles can be obtained by any method known to the one skilled in the art, e.g. by co-transfection of 293 HEK cells, by the herpes simplex virus system and by the baculovirus system. The vector titers are usually expressed as viral genomes per mL (vg/mL).

In one embodiment, the expression vector comprises regulatory sequences, especially a promoter sequence. Such promoters can be natural or synthetic (artificial) promoters, inducible or constitutive.

In one embodiment, the promoter is an ubiquitous promoter or having a low tissue-specificity. As an example, the expression vector can harbor the phosphoglycerate kinase 1 (PGK), EF1, (β-actin, CMV promoter.

In a preferred embodiment, the promoter sequence is chosen in order to adequately govern the expression of the nucleic acid sequence placed under its control, in terms of expression level, but also of tissue specificity. In one embodiment, the expression vector comprises a muscle specific promoter. Such a promoter allows a robust expression in the skeletal muscles, and possibly in the cardiac muscle as well as in the diaphragm. Examples of suitable promoters known by the skilled person are e.g. the desmin promoter, the muscle creatine kinase (MCK) promoter, the CK6 promoter, and the Syn promoter. Another promoter is the synthetic promoter C5-12 (spC5-12) as shown in sequences SEQ ID NO: 1 or 2 (nucleotides 215 to 537), which allows a robust expression in skeletal and cardiac muscles.

A non-exhaustive list of other possible regulatory sequences is:
  a polyadenylation signal, e.g. the polyA of the gene of interest, the polyA of SV40 or of beta hemoglobin (HBB2), advantageously in 3' of the sequence encoding the functional microdystrophin; The poly A of SV40 is disclosed in sequences SEQ ID NO: 1 (nucleotides 4223 to 4353) and SEQ ID NO: 2 (nucleotides 4226 to 4356);
  sequences for transcript stabilization, e.g. intron 1 of hemoglobin (HBB2);
  enhancer sequences;
  miRNA target sequences, which can inhibit the expression of the sequence encoding the functional dystrophin in non target tissues, in which said expression is not desired, for example where it can be toxic. Preferably, the corresponding miRNA is not present in the skeletal muscles, and possibly not in the diaphragm nor in the heart.

According to one embodiment, the gene therapy product comprises an expression vector, advantageously an AAV vector harboring the sequence SEQ ID NO: 1 or SEQ ID NO: 2, advantageously SEQ ID NO: 1. As mentioned above, the invention also encompasses "substantially homologous" sequences, that is, displaying about 60% homology, more preferably about 70% homology, even more preferably about 80% homology, more preferably about 90% homology, even more preferably about 95% homology, and even more preferably about 97%, 98% or even 99% homology to the sequence SEQ ID NO: 1 or 2.

According to the present invention, the composition comprises at least said gene therapy product, and possibly other active molecules (other gene therapy products, chemical molecules, peptides, proteins . . . ), dedicated to the treatment of the same disease or another disease.

According to a specific embodiment, said composition does not comprise any immunosuppressive agent.

The present invention then provides pharmaceutical compositions comprising a nucleic acid of the invention, or the vector of the invention. Such compositions comprise a therapeutically effective amount of the therapeutic (the nucleic acid or vector of the invention), and a pharmaceutically acceptable carrier. In a specific embodiment, the term "pharmaceutically acceptable" means approved by a regulatory agency of the Federal or a state government or listed in the U.S. or European Pharmacopeia or other generally recognized pharmacopeia for use in animals, and humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsions, sustained-release formulations and the like. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the subject.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to release pain at the site of the injection.

In one embodiment, the composition according to the invention is suitable for administration in humans. The composition is preferably in a liquid form, advantageously a saline composition, more advantageously a phosphate buffered saline (PBS) composition or a Ringer-Lactate solution.

The amount of the therapeutic (i.e. a nucleic acid or a vector) of the invention which will be effective in the treatment of dystrophic diseases can be determined by standard clinical techniques. In addition, in vivo and/or in vitro assays may optionally be employed to help predict optimal dosage ranges. The precise dose to be employed in the formulation will also depend on the route of administration, the weight and the seriousness of the disease, and should be decided according to the judgment of the practitioner and each patient's circumstances.

Suitable administration should allow the delivery of a therapeutically effective amount of the gene therapy product to the target tissues, especially skeletal muscles and possibly diaphragm and heart. In the context of the invention, when the gene therapy product is a viral vector comprising a nucleic acid sequence encoding a functional microdystrophin, the therapeutic dose is defined as the quantity of viral particles (vg for viral genomes) containing the microdystrophin sequence, administered per kilogram (kg) of the subject.

Available routes of administration are topical (local), enteral (system-wide effect, but delivered through the gastrointestinal (GI) tract), or parenteral (systemic action, but delivered by routes other than the GI tract). The preferred route of administration of the compositions disclosed herein is parenteral which includes intramuscular administration (i.e. into the muscle) and systemic administration (i.e. into the circulating system). In this context, the term "injection" (or "perfusion" or "infusion") encompasses intravascular, in particular intravenous (IV), and intramuscular (IM) administration. Injections are usually performed using syringes or catheters.

In one embodiment, systemic delivery of the composition comprises administering the composition near a local treatment site, i.e. in a vein or artery nearby a weakened muscle. In certain embodiments, the invention comprises the local delivery of the composition, which produces systemic effects. This route of administration, usually called "regional (loco-regional) infusion", "administration by isolated limb perfusion" or "high-pressure transvenous limb perfusion" has been successfully used as a gene delivery method in muscular dystrophy (Zheng Fan et al. (2012, Molecular Therapy 20(2), 456-461).

According to one aspect, the composition is administered to an isolated limb (loco-regional) by infusion or perfusion. In other words, the invention comprises the regional delivery of the composition in a leg and/or arm by an intravascular route of administration, i.e. a vein (transveneous) or an artery, under pressure. This is usually achieved by using a tourniquet to temporarily arrest blood circulation while allowing a regional diffusion of the infused product, as e.g. disclosed by Toromanoff et al. (2008, Molecular Therapy 16(7):1291-99), Arruda et al. (2010, Blood 115(23):4678-88) and Fan et al. (2012, Molecular Therapy 20(2), 456-461).

In one embodiment, the composition is injected in a limb of the subject. In one embodiment, the subject is a mammal, preferably a human, a dog or a nonhuman primate. When the subject is a human, the limb can be the arm or the leg. According to one embodiment, the composition is administered in the lower part of the body of the subject, e.g. below the knee, or in the upper part of the body of the subject, e.g., below the elbow.

In one embodiment, the composition is administered to a peripheral vein, e.g. the cephalic vein. The volume of the composition to be infused can be in a range that varies between about 5 and 40% of the limb volume. The typical dose can vary between 5 and 30 ml/kg of body weight. In one embodiment, the pressure to be applied (tourniquet pressure or maximum line pressure) is below 100 000 Pa, advantageously below 50 000 Pa. In a preferred embodiment, the pressure applied is around 300 torr (40 000 Pa).

In one embodiment, the blood circulation of the limb is stopped using a tourniquet that is tightened for several minutes to more than one hour, typically between about 1 and 80 minutes, for example about 30 minutes. In a preferred embodiment, the tourniquet was applied before, during and after the administration, for example about 10 minutes prior to, about 20 minutes during and about 15 min after the infusion. More generally, the pressure is applied for several minutes, typically between about 1 and 80 minutes, for example about 30 minutes. In a preferred embodiment, the pressure is applied before, during and after the administration, for example about 10 minutes prior to, about 20 minutes during and about 15 minutes after the infusion.

In one embodiment, the average flow rate is comprised between 5 and 150 ml/min, advantageously between 5 and 80 ml/min, for example 10 ml/min. Of course, the flow rate also determines the time period during which the blood circulation is stopped and the pressure applied.

In the context of a loco-regional administration, the dose injected may vary between $10^{12}$ and $10^{14}$ vg/kg of the patient body, preferably between $10^{12}$ and $10^{13}$ vg/kg.

A preferred method of administration according to the invention is systemic administration. Systemic injection opens the way to an injection of the whole body, in order to reach the entire muscles of the body of the subject including the heart and the diaphragm and then a real treatment of these systemic and still incurable diseases. In certain embodiments, systemic delivery comprises delivery of the composition to the subject such that composition is accessible throughout the body of the subject.

According to a preferred embodiment, systemic administration occurs via injection of the composition in a blood vessel, i.e. intravascular (intravenous or intra-arterial) administration. According to one embodiment, the composition is administered by intravenous injection, through a peripheral vein.

The systemic administration is typically performed in the following conditions:

a flow rate of between 1 to 10 mL/min, advantageously between 1 to 5 mL/min, e.g. 3 mL/min;

the total injected volume can vary between 1 and 20 mL, preferably 5 mL of vector preparation per kg of the subject. The injected volume should not represent more than 10% of total blood volume, preferably around 6%.

When systemically delivered, the composition is preferably administered with a dose less than or equal to $10^{15}$ vg/kg or even $10^{14}$ vg/kg, advantageously between $10^{12}$ vg/kg and $10^{14}$ vg/kg, more advantageously between $5.10^{12}$ vg/kg and $10^{14}$ vg/kg, e.g. 1, 2, 3, 4, 5, 6, 7, 8 or $9.10^{13}$ vg/kg. A lower dose of e.g. 1, 2, 3, 4, 5, 6, 7, 8 or $9.10^{12}$ vg/kg can also be contemplated in order to avoid potential toxicity and/or immune reactions. As known by the skilled person, a dose as low as possible given a satisfying result in term of efficiency is preferred.

In a specific embodiment, the treatment comprises a single administration of the composition.

As it will be illustrated in the examples below, the administration of the gene therapy product according to the invention is not believed to be associated with adverse immune reactions. Therefore, and according to one embodiment, said administration is not combined with any further or extra immunosuppressive treatment (immunosuppression).

In one embodiment, the presence of the gene therapy product and/or the expression of the functional microdystrophin, as well as the associated therapeutic benefits, are observed for up to 1 month, or 3 months or 6 months or even 1 year, 2 years, 5 years, 10 years, or even more the whole life of the subject.

According to the invention, the subject is a mammal, preferably a human or a dog, but can also be a mouse, a rat or a nonhuman primate.

"Dystrophic disease" means a disease linked to a defect in the dystrophin gene. This defect can be deletions or mutations leading to low level of expression or absence of expression, introduction of a premature stop codon in the open reading frame, or the production of an inactive protein. Preferred dystrophic diseases are Duchenne and Becker muscular dystrophy (DMD/BMD) caused by mutations of the dystrophin gene. Said mutations can result in the absence or a low level of dystrophin expression, or in the production of a partially or fully inactive, possibly truncated protein.

Subjects that could benefit from the compositions of the invention include all patients diagnosed with a muscular dystrophy or at risk of developing such a muscular dystrophy. A subject to be treated can then be selected based on the identification of mutations or deletions in the dystrophin gene by any method known to the one skilled in the art, including for example sequencing of the dystrophin gene, and/or through the evaluation of the dystrophin level of expression or activity by any method known to the one skilled in the art. Therefore, said subjects include both subjects already exhibiting symptoms of a dystrophic disease and subjects at risk of developing said disease. In one embodiment, said subjects include subjects already exhibiting symptoms of a dystrophic disease. In another embodiment, said subjects are ambulatory patients and early non-ambulant patients.

Such compositions are notably intended for gene therapy, particularly for the treatment of Duchenne muscular dystrophy (DMD) or Becker muscular dystrophy (BMD), advantageously DMD.

A first target of the invention is to provide a safe (not toxic) treatment. A further aim is to provide an efficient treatment which allows to postpone, slow down or prevent the development of the disease, and possibly to ameliorate the phenotype of the patient which can be easily monitored at the clinical level.

In a subject, the composition according to the invention can be used:

for ameliorating muscular function. Of particular interest are the skeletal muscles, but also the cardiac muscle and the diaphragm.

for ameliorating gait;
for ameliorating cardiac function;
for ameliorating respiratory function; and/or
for prolonging survival, more generally to ameliorate the quality and the expectancy of life.

According to one aspect, the invention concerns a method for ameliorating muscular function, gait, cardiac function and/or respiratory function, and/or for prolonging survival, advantageously without adverse (cellular and/or humoral immune response), comprising administering to a subject in need thereof a therapeutic quantity of a gene therapy product as disclosed above.

An amelioration of said functions can be evaluated based on methods known in the art, e.g.:

assessment of the percentage of muscle fibers expressing the dystrophin protein;
walking tests;
assessment of strength by dynamometer measurements;
assessment of motor function of a precise limb by motor function measurements;
assessment of global activity using a movement monitor;
assessment of gait by accelerometric recording in 3 axes;
assessment of cardiac function by echocardiographic, Doppler analyses and Speckle tracking analysis;
assessment of respiratory function by evaluation of diaphragm kinetics;
assessment of quality and expectancy of life by clinical score.

As illustrated in the examples, the claimed treatment allows improving the clinical state and the various parameters disclosed above in comparison with an untreated subject. According to one embodiment, the present invention concerns a method of treatment of a dystrophic disease comprising administering to a subject the gene therapy product as disclosed above, wherein:

at least 30% of the muscle fibers, advantageously 40%, more advantageously at least 50% of the muscle fibers express the dystrophin protein; and/or a clinical score is maintained at a level corresponding to at least 50% of the score of a healthy subject, advantageously at least 60% or even 70%.

Advantageously, said effects are observed for up to 1 month after administration, or 3 months or 6 months or 9 months, more advantageously for up to 1 year after administration, 2 years, 5 years, 10 years, or even more the whole life of the subject.

As known in the art, the level of dystrophin expression in muscles is easily determined by the skilled person, advantageously by immunohistochemistry, e.g. by immunostaining of muscular biopsies with an anti-Dystrophin antibody as disclosed above. The calculation of clinical scores is also routine for the skilled person. As detailed above in relation with dogs, this score can be calculated based on dysphagia, breathing, ptyalism and global activity. Concerning patients, Bushby and Connor have e.g. listed clinical outcome measures for trials in Duchenne muscular dystrophy (Clin Investig (Lond). 2011; 1(9): 1217-1235).

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

The disclosures of each and every patent, patent application, and publication cited herein are hereby incorporated herein by reference in their entirety.

Without further description, it is believed that one of ordinary skill in the art can, using the preceding description and the following illustrative examples, make and utilize the compounds of the present invention and practice the claimed methods.

EXPERIMENTAL EXAMPLES

The invention is further described in detail by reference to the following experimental examples and the attached figures. These examples are provided for purposes of illustration only, and are not intended to be limiting.

The results presented below have been obtained in the GRMD (Golden Retriever Muscular Dystrophy) dog model. It is the best animal model for dystrophic pathologies, in order to evaluate the potential of a gene therapy product, in terms of efficiency (therapeutic dose, stability, toxicity, . . . ) but also of immune response, before clinical trials.

BRIEF DESCRIPTION OF THE DRAWINGS

A/ Muscular biopsies obtained 3 months post rAAV2/8-SPc5.12-cMD vector administered by intravenous systemic delivery into the GRMD2 dog (ICI).
  a/ m. biceps femoris before injection
  b/ healthy dog
  c/ m. extensor carpi radialis right:
    82% of cMD +fibers (cMD detected in 82% of the fibers)
    2.8 vg/dg (vector genome per diploid genome)
  d/ m. extensor digitorum communis right:
    59% of cMD +fibers (cMD detected in 59% of the fibers)
    4.1 vg/dg
  e/ m. extensor carpi radialis left:
    62% of cMD +fibers (cMD detected in 62% of the fibers)
    6.2 vg/dg
  f/ m. extensor digitorum communis left:
    66% of cMD +fibers (cMD detected in 66% of the fibers)
    2.6 vg/dg B/ Muscular biopsies obtained 8 months post rAAV2/8-SPc5.12-cMD vector administered by intravenous systemic delivery into the GRMD2 dog (ICI):
  a/ m. biceps femoris right:
    58% of cMD+fibers (cMD detected in 58% of the fibers)
    1.0 vg/dg
  b/ m. biceps femoris left:
    56% of cMD +fibers (cMD detected in 56% of the fibers)
    0.8 vg/dg

MATERIALS AND METHODS

1/ Animals

The evaluation of a fully systemic injection of the microdystrophin vector (rAAV2/8-SPc5.12-cMD) has been performed in the GRMD dog model (Kornegay et al., Mamm Genome, 2012). Selected male dogs were genotyped for the DMD mutation, which consists of a single base change in the 3' consensus splice site (A>G) of intron 6 of the dystrophin gene that provokes inaccurate mRNA processing.

Dogs were treated as shown in Table 1 below (without immunosuppression):

| | | | | | |
|---|---|---|---|---|---|
| $1^E14$vg/kg | Long term | IMAGE | μDys 1 | 6 Nov. 2013 | Still alive (17 months post-inj°) |
| | | ICI | μDys 2 | 6 Jan. 2014 | Still alive (15 months post-inj°) |
| | 7-8 months post-injection | ICE-T | μDys 3 | 28 Aug. 2013 | 16 Apr. 2014 |
| | | JAFFAR | μDys 4 | 16 Sep. 2014 | May 2015 |
| | | JACADI | μDys 5 | 3 Nov. 2014 | July 2015 |

Control dogs correspond to non injected GRMD dogs and healthy dogs.

2/ Microdystrophin vector

The rAAV2/8-SPc5.12-cMD vector encodes an mRNA sequence-optimized canine dystrophin (cMD) under the control of a muscle-specific promoter (SPc5.12).

Figure 1:
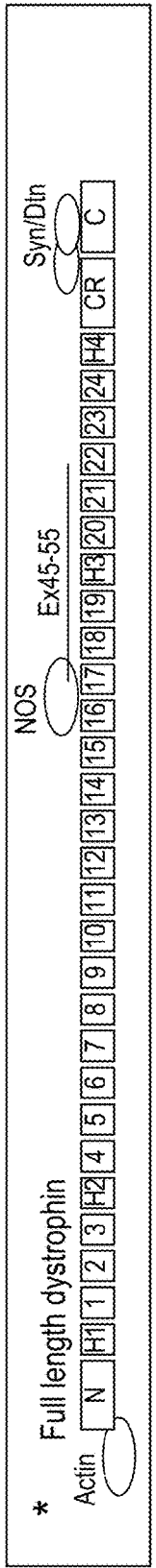
FIG. 1: Scheme of the full-length dystrophin (A), of various microdystrophins (B) and of the expression construct (C).
Figure 1:
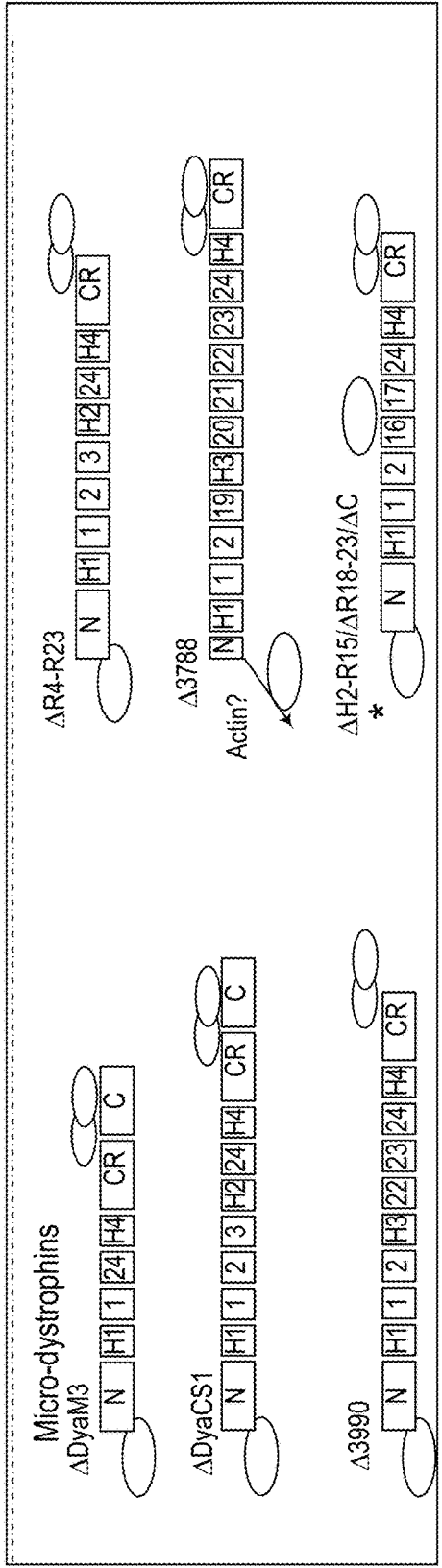
Figure 1:
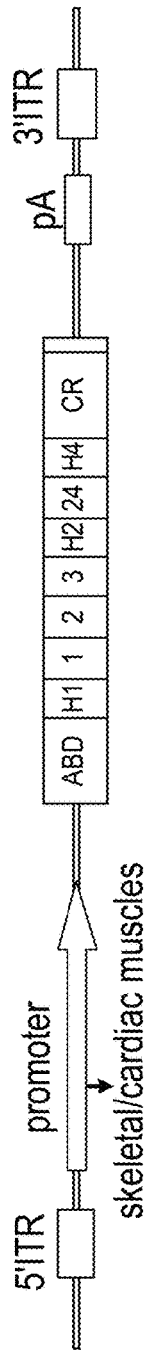

The construction of canine-specific, mRNA sequence-optimized cMD cDNA, incorporated deletions of rod domains 4-23 and exon 71-78 of the CT domain of dystrophin (AR4-R23; FIG. 1), containing the last three amino acids of exon 79 of dystrophin followed by three stop codons and incorporating the SV40 poly adenylation site. cDNA sequence was modified to include a consensus Kozak sequence. An mRNA sequence was optimized based on transfer RNA frequencies in human and GC content was increased to promote RNA stability. mRNA sequence optimization of microdystrophin (GENEART, Regensburg, Germany) resulted in the GC content being increased from 48% to 61% in the canine dystrophin and 23.6% of codons being modified as well. The size of the cMD gene cDNA is 3603 bp and the flanking inverted terminal repeat (ITR)-containing transgene cassette size of this vector is 4643 bp, which corresponds to 99.2% of the 4682 bp of wild-type-AAV2 genome length. 5'- and 3'-untranslated regions of the dystrophin gene were removed to decrease the flanking ITR size of the dystrophin cassette. Expression was under the control of the muscle-specific synthetic promoter (SPc5-12) (Wang, B., et al., Gene Ther, 2008. 15(22): p. 1489-99).

This expression cassette (SEQ ID NO: 2 including the AAV ITR, the Spc512 promoter, the canine MD cDNA and the SV40 PolyA) was demonstrated to result in widespread and stable dystrophin expression after intramuscular injections in the Duchenne beagle-based CXMDJ model (Koo, T., et al., J Gene Med, 2011. 13(9): p. 497-506). In addition, this construct improved muscle pathology and reduction of inflammatory responses in the target muscle tissue.

3/ Preparation of rAAV2/8-SPc5.12-cMD

The recombinant adeno-associated virus vector containing the canine microdystrophin cDNA regulated by the SPc5-12 promoter, rAAV2/8-SPc5.12-cMD, was produced in a baculovirus/SP9 system. Two baculovirus batches were generated, one expressing rep (encoding the AAV2 Rep protein) and cap (encoding the AAV8 Cap protein) AAV genes and the second being the AAV2 transfer vector. The viruses were produced, banked, and used to co-infect SF9 cells in 200-liter single-use bioreactor (Sartorius). After a three-day culture, cells are harvested, lysed, and the lysate processed by clarification, purification on an immunoaffinity column, concentration through tangential flow filtration, formulation, sterile filtering and filling. Purification is based on a commercial gel (AVB from GE Healthcare) carrying a single-chain antibody binding AAV1, AAV2, AAV3, AAV5, AAV6, and AAV8. The process has an overall yield of >20%, and generates 145 units of 4.5 ml product with a viral titer >$10^{13}$ vg/ml.

4/ Systemic administration

GRMD dogs have been injected by systemic delivery with the therapeutic candidate (rAAV2/8-SPc5.12-cMD) vector. This pilot cohort was administered with $10^{14}$ vg/kg (total of around $5 \times 10^{14}$ vg/animal). The simple systemic injection was performed through a peripheral vein, in a cannulated cephalic vein, at a flow rate of 3 mL/min. Total injected volume was around 25 mL of vector preparation (5 ml/kg) representing 6% total blood volume (10% being the recommended upper limit), which turned out to be very well tolerated.

The experimental animals were injected at the age of 2 months and are followed as shown in Table 1. They all were prescreened for the absence of AAV8 neutralizing factors in the serum. Prior the intravenous (IV) injection of the vector, GRMD dogs that exhibited profound weakness and/or swallowing impairment were discarded from the experiment. Immunosuppressive regiments were never used and the only medical care provided was restricted to maintain comfort and wellbeing of the animals. Appropriate regulatory documents (ethics and GMO handling) were obtained in due time. All procedures are carried out accordance with the Guide for the Care and Use of Laboratory Animals and approved by the ad hoc Animal Use and Care Committee.

5/ Evaluation of the systemic treatment

Morbidity and mortality are assessed twice daily. Animals found dead would be submitted to necropsy in the presence of the pathologist and tissue samples collected when appropriate in attempt to systematically determine the cause of death.

Clinical and biological tolerance of the protocol

In all dogs, clinical laboratory parameters including electrolytes, kidney and liver function tests and complete blood counts are monitored regularly after injection. The clinical status of each dog, including cardiac, respiratory, digestive, locomotors and neurologic functions, are also carefully and weekly evaluated all along the protocol.

Assessment of vector shedding and vector biodistribution by Q-PCR

Vector shedding and vector biodistribution by Q-PCR are performed regularly until euthanasia on urine, serum, intermediate muscle biopsies, major skeletal muscles from the 4 limbs among flexors and extensors, heart and diaphragm, liver, spleen, kidneys, lymph nodes and testis. Extraction of rAAV DNA from fluids is done using the Qiamp Viral RNA mini-kit (Qiagen).

rAAV is extracted from 140 µL of serum. 1/8 of the extraction (10 µL) is used for Q-PCR analysis. Extraction of genomic DNA (gDNA) from tissues is done using the Gentra Puregene kit (Qiagen) and Tissue Lyzer II (Qiagen). The concentration of each gDNA sample is determined using a nano-spectrophotometer (Implen).

Quantitative PCR is conducted on a StepOne Plus (Applied Biosystem) using 50 ng of gDNA in duplicates or 10 µL of fluid extracts. Vector copy numbers is determined using primers and probe designed to specifically amplify the SPc5.12-cMD cassette. gDNA copy numbers is determined using primers and probe designed to amplify the canine glucuronidase gene. For each sample, Ct (cycle threshold) values are compared with those obtained with different dilutions of linearized standard plasmids (containing either the SPc5.12-cMD cassette or the canine glucuronidase gene). Results are expressed in vector genome per diploid genome (vg/dg). For fluids, only the transgene specific Q-PCR is performed and results are expressed in vector genome per µl of fluid extracted. The absence of Q-PCR inhibition in the presence of gDNA is previously checked by analyzing 10 µL of fluid extract or 50 ng of gDNA extracted from spleen, testis, liver, kidney or skeletal muscle, spiked with different dilutions of standard plasmid.

Assessment of transgene expression in different tissues by Q-RT-PCR

Microdystrophin expression is assessed by Q-RT-PCR in multiple skeletal muscles, heart and diaphragm, liver, spleen, and any other tissue exhibiting high vector copy number. Briefly, total RNA is extracted from muscles, liver and spleen with TRIzol reagent (Invitrogen) and treated with RNAse-free DNAse I from the TURBO DNA-free kit (Ambion) according to the manufacturer's instructions. Reverse transcription is performed using random primers and an M-MLV reverse transcriptase (Invitrogen). A negative control without reverse transcriptase (RT-) is processed for each sample. Quantitative PCR is conducted on a StepOne Plus (Applied Biosystem) diluted cDNA in duplicates. The relative quantification of the cMD messengers is determined using primers designed to specifically amplify this sequence. The results are normalized by a Q-PCR analysis of the canine RPL32 (Ribosomal Protein L32) messenger, known to be similarly expressed in the different tissues of dog (Peters, I. R., et al., Vet Immunol Immunopathol, 2007. 117(1-2): p. 55-66). The absence of Q-PCR inhibition in the presence of cDNA of muscle, liver and spleen is checked by analyzing diluted cDNA spiked with different dilutions of standard plasmid.

For each sample, Ct (cycle threshold) values are compared with those obtained with different dilutions of standard plasmids (containing the cMD expression cassette or the sequence of the canine RPL32 messenger). Results are expressed in relative quantities (RQ):

$$RQ = 2^{-\Delta ct} = 2^{-(Ct\ target - Ct\ endogenous\ control)}$$

Analysis of Dystrophin expression by Western blot

Using a specific Western-Blot analysis, the expression of microdystrophin in different muscles of the injected dogs is evaluated:

In several skeletal muscles, as well as the heart and the diaphragm, sampled at euthanasia, In liver, spleen and any other tissues in which a high level of transgene copy numbers would be found, at euthanasia.

Total proteins are extracted from tissue samples. Protein extracts are separated on SDS-PAGE, transferred on a nitrocellulose membrane. After Red Ponceau staining, membranes are blocked in 5% skim milk in TBS and hybridized with the antiDystrophin MANEX1011C antibody and with secondary anti-mouse IgG HRP-conjugated antibody.

Analysis of Dystrophin expression by immunohistochemistry

By immunochemistry, microdystrophin expression is evaluated in the skeletal muscles of the injected dogs:

In intermediate muscular biopsies,

In all skeletal muscles, as well as the heart and the diaphragm, sampled at euthanasia, In liver, spleen, testes, kidneys and lymph nodes, sampled at euthanasia. microdystrophin expression and localization are assessed by immunohistochemistry. microdystrophin polypeptide immunostaining is performed on transverse sections of each muscle using the mouse anti-Dystrophin antibody from Novocastra (NCL-DYSB). The restoration of the Dystrophin-associated proteins is evaluated by immunostaining of β-dystroglycan, β-sarcoglycan, gamma-sarcoglycan and Utrophin, including colocalization with laminin at the sarcolemal membrane.

Assessment of the local pathological pattern in the muscles

Pathology assessment is key to address the actual benefit of the gene therapy product at the target tissue level. Using morphometric analyses, the EC Board-certified pathologist evaluates the pathological pattern in the skeletal muscles of the injected dogs. These analyses are done on postural muscles with a majority of type I fibers (proximal limb muscles, paravertebral muscles); locomotor muscles with a majority of type II fibers (flexor and extensors from distal limb muscles); respiratory muscles, diaphragm, intercostal and masticatory muscles. Heart is evaluated extensively as well with the specific difficulty to apprehend fibers diameter due to unparalleled orientation.

Endomysial fibrosis is evaluated after immunohistochemical revelation of Collagen I (immunoperoxydase assay) and automatic measurement of the percentage of the labeled areas.

Total fibrosis is evaluated after immunohistochemical revelation of Collagen I (immunoperoxydase assay), on the same slides than endomysial fibrosis. An automatic measurement of the percentage of the total labeled areas is also performed.

Perimysial fibrosis is calculated by the difference between total fibrosis and endomysial fibrosis in the same fields of muscular tissue.

Anocytosis (variation of fibers diameter) is evaluated by manual morphometry: determination of the minimum fiber diameter on at least 200 myofibers and six fields per analyzed muscle cross-section.

Necrosis is evaluated by measurement of calcium accumulation, by an Alizarin Red staining. The percentage of labeled areas is measured after manual threshold.

Regeneration is evaluated after immunohistochemical revelation myotubes with an antibody specific of a developmental Myosin Heavy Chain isoform (immunoperoxydase assay). The percentage of labeled areas is measured after manual threshold.

Inflammation is evaluated after immunohistochemical revelation of T and B lymphocytes and macrophages on the same slide (immunoperoxydase assay). The percentage of labeled areas is determined after manual threshold.

Assessment of the pathological pattern in the different tissues

Potential adverse side effects due to off target tissues (liver, spleen, kidney, . . . ) is evaluated using HE staining and anatomopathology expertise in the different tissues of the dogs at euthanasia.

NMR imaging and spectroscopy indices of skeletal muscles

Non-invasive muscle imaging and spectroscopy indices are performed a week before euthanasia. The dogs are sent to Institute of Myology, Paris (Pierre Carlier's team) and subjected to a 3T Siemens Trio scanner Nuclear Magnetic Resonance (NMR) to quantitatively and serially describe the dystrophic muscle abnormalities compared to untreated and healthy animals. In addition to that, P31 spectroscopy of the extensor carpi radialis is realized at 4T in a Bruker biospec scanner. Each individual measurement is positioned relative to the reference data during previous NMR studies of disease progression in groups of untreated and healthy dogs Thibaud, J. L., et al., Neuromuscul Disord, 2012. 22 Suppl 2: p. S85-99; Wary, C., et al., NMR Biomed, 2012. 25(10): p. 1160-9. Thoracic and pelvic/fore limbs are imaged in a 3T scanner. Standard and fat-saturated T1-, T2- and proton-density-weighted images are acquired as described in Thibaud, J. L., et al. (Neuromuscul Disord, 2007. 17(7): p. 575-84). A measurement of T1 and a two-hour kinetic study of muscle enhancement after gadolinium-chelate injection are also performed. Ten indices that differ between healthy and untreated GRMD dogs have been identified, which allow interpreting the effect of the gene therapy treatment on large muscle territories.

Functional assessment: clinical grading

Clinical examination is also performed twice daily and includes food and water consumption, activity (global comportment, response to external stimuli) and physical appearance (face, fur, limbs). A full examination with body weight is performed on all animals during each anesthesia.

The general clinical status of the animals with respect to the muscle disease is evaluated by a clinical grading done weekly after injection, using a previously published protocol (Rouger, K., et al., Am J Pathol, 2011. 179(5): p. 2501-18). This evaluation includes 11 locomotion criteria and 6 items related to the general health status (including dysphagia, ptyalism, global activity and breathing). Each item is scored from 0 to 2, with 0 corresponding to the absence of symptoms and 2 to maximum severity. The global clinical score is expressed as the percentage of the maximum clinical score (defined as 100% for a healthy dog) and a tendency curve (mobile means order 3) is built to represent the clinical score evolution. The clinical score evolution obtained in the injected dogs is compared to the clinical score evolution of non-injected GRMD dogs.

Functional assessment: Gait analysis (muscular function)

Gait analysis quantified by Locometrix is performed twice a month. Locometrix® is a 3D accelerometric device composed of 3 orthogonally positioned accelerometers. This construction allows the recording of the accelerations along the dorso-ventral, cranio-caudal and medio-lateral axes of the dogs. Speed, stride frequency, stride length, regularity, total power, dorso-ventral power, cranio-caudal power, medio-lateral power and force can be analyzed with this device, and several of these indices are modified during the progression of the disease in GRMD dogs (Barthelemy, I., et al., BMC Musculoskelet Disord, 2011. 12: p. 75).

Functional assessment: Cardiac function evaluation

Cardiac function of the treated dogs is evaluated monthly using echocardiographic and Doppler analysis, a sensitive approach allowing the detection of contractility defects.

Data acquisition:

Conventional echocardiography and 2D color tissue Doppler imaging (TDI) are performed on conscious dogs in standing position monitored with a continuous ECG, using a Vivid 7 ultrasound unit equipped with 5-7.5 and 2-5 MHz phased-array transducers (GE, Waukesha, Wis.), according to the recommendations from the American College of Veterinary Internal Medicine (Thomas, W. P., et al., J Vet Intern Med, 1993. 7(4): p. 247-52). All data are transferred for offline analysis using a specific software (Echo Pac 5.4, GE) by two examiners who are unaware of the clinical status of the dogs. Several parameters are measured for the assessment of myocardial contractility as described below.

Conventional parameters: Left ventricular (LV) dimensions, posterior wall and interventricular septal wall thicknesses are measured. Left ventricular fractional shortening and ejection fraction (Teichholz method) are calculated. Pulsed Doppler of the mitral valve inflow are used for measuring the ratio of early to late diastolic flow velocity (E/A).

Tissue Doppler imaging: Measurement of radial myocardial velocities and strain rate are obtained from a short-axis view at the level of the papillary muscles in the posterior wall and an apical 4-chamber view at the level of the basal portion of the septal and lateral walls. Speckle tracking imaging: In a short-axis view, segmental strains in each of the 5 predefined segments are measured. Mean circumferential and radial are determined by calculating manually the mean of the measurements obtained. In the 4 chambers view, global longitudinal strains are measured automatically with a program that integrates the measurements derived from the analysis of 6 automatically detected segments. Pre injection data and mock injected GRMD serve as references.

Functional assessment: respiratory function evaluation

Respiratory function is evaluated monthly and is done by using thoracic radioscopic acquisitions performed on conscious dogs. After extraction of the end-expiratory and end-inspiratory images, 2 indices are calculated: the caudal retraction index and the diaphragm range of motion. These 2 indices are correlated with the retraction and the mobility of the diaphragm, which are modified during disease progression in GRMD dogs (Barthelemy, I., et al., Myology congress, 2011). The results obtained in the GRMD dogs are positioned relative to the results obtained in non-injected untreated animals.

Follow up of the immune responses

During the entire study, blood samples (plasma, serum and peripheral blood mononuclear cells-PBMC) from dogs enrolled in the study are harvested to monitor the:

humoral immune response against rAAV8
humoral immune response against microdystrophin
cellular immune response against rAAV8
cellular immune response against microdystrophin
inflammatory immune response in the early times after injection Blood samples are handled according to the French L2 biosafety requirements and are processed for hematology and clinical biochemistry. Dedicated serum samplings are regularly obtained for the following immunology assessments: (i) anti-AAV antibodies and anti-dystrophin antibodies; (ii) inflammatory cytokines measurement by Luminex; (iii) complement activation. Whole blood was also collected prior and after treatment for isolation of the peripheral blood mononuclear cells (PBMC) and subsequent monitoring a potential cellular immune response against AAV and/or dystrophin polypeptide.

Humoral immune responses to rAAV8 vector:

Dog sera is evaluated at different time points post-vector injection: (i) for the presence of IgG, and IgM specific to rAAV8 detected by customized ELISA; (ii) for the rAAV8 neutralizing capacity revealed by customized neutralizing assay.

Humoral immune responses to Dystrophin:

The detection of IgG anti-Dystrophin antibodies is routinely performed by Western-Blot analysis. Briefly, cellular extracts containing canine dystrophin protein are subjected to SDS-PAGE, and then transferred to a Hybond ECL nitrocellulose membrane. After an overnight saturation, membranes are incubated with experimental canine sera from injected animals. Subsequently, detection is performed by hybridization with peroxydase conjugated rabbit anti-dog IgG antibody, followed by enhanced chemiluminescence detection. Positive control consists in anti-Dystrophin MANEX 1011C antibody (Wolfson Center for Inherited Neuromuscular Diseases).

The cellular immune responses to AAV8 and dystrophin polypeptide are evaluated as follows:

Briefly, IFN-γ ELISPOT assays are performed with lentiviral vectors (LV) encoding for either VP proteins of AAV8 or canine dystrophin polypeptide. LV vectors are used to transduce PBMC. A complementary approach using an overlapping peptide library covering the canine sequence of canine dystrophin polypeptide is also used to stimulate lymphocytes.

Inflammatory immune responses (cytokines) are quantified by Luminex technology before and at different time points post-vector administration looking at IL2, IL4, IL6, IL8, IL10, IL15, IFN and TNF.

Figure 2:
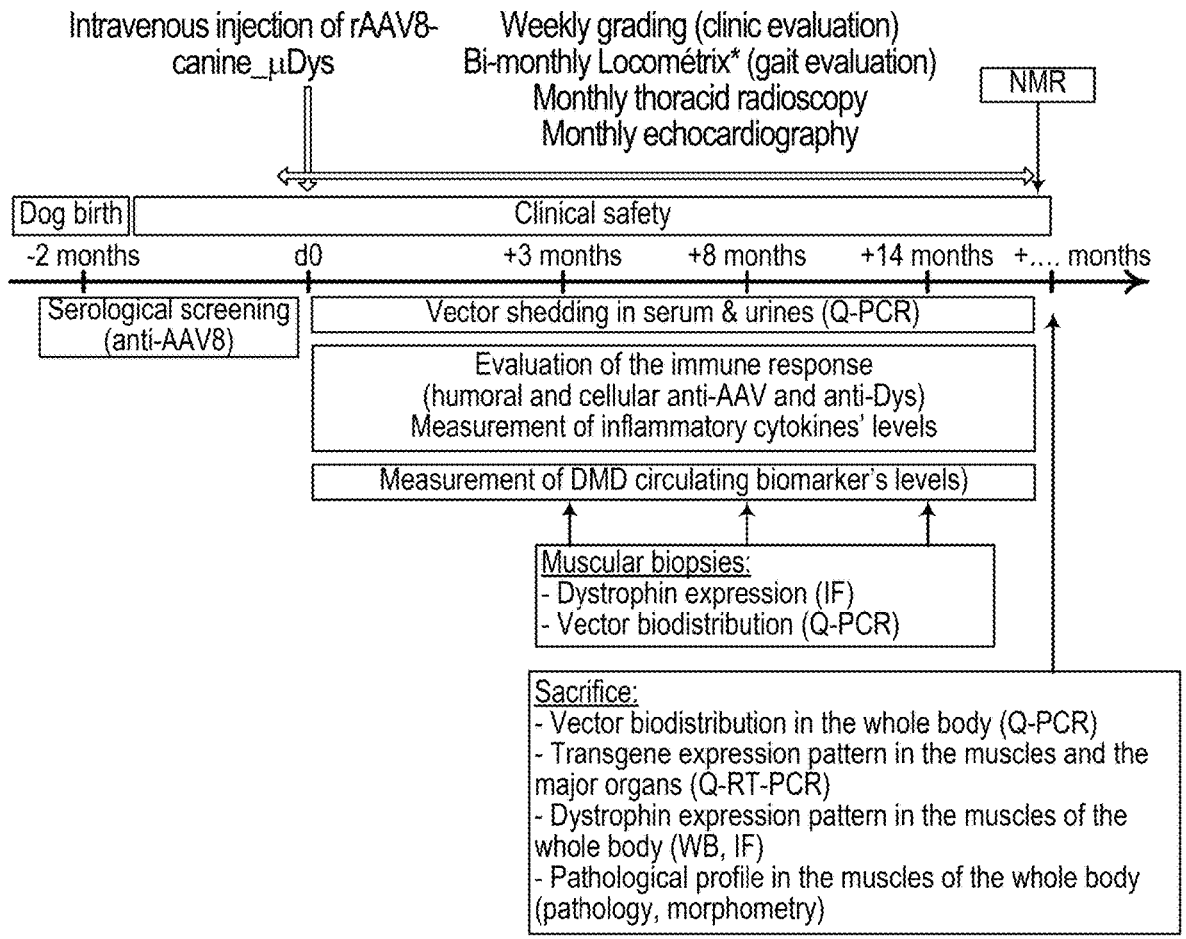
FIG. 2: Study plan—General scheme of the systemic treatment in GRMD dogs.

Results:

As shown on FIG. 2, 2-month old GRMD dogs have been injected with $1 \times 10^{14}$ vg/kg of the rAAV2/8-SPc5.12-cMD vector described above, by simple systemic injection through a peripheral vein. No clinical nor biochemical nor hematology adverse effects were ever detected immediately nor up to several months post vector administration.

Muscular biopsies:

Intermediate biopsies from several different muscles were obtained for the GRMD dogs, 3 and 8 months post systemic injection.

Figure 3:
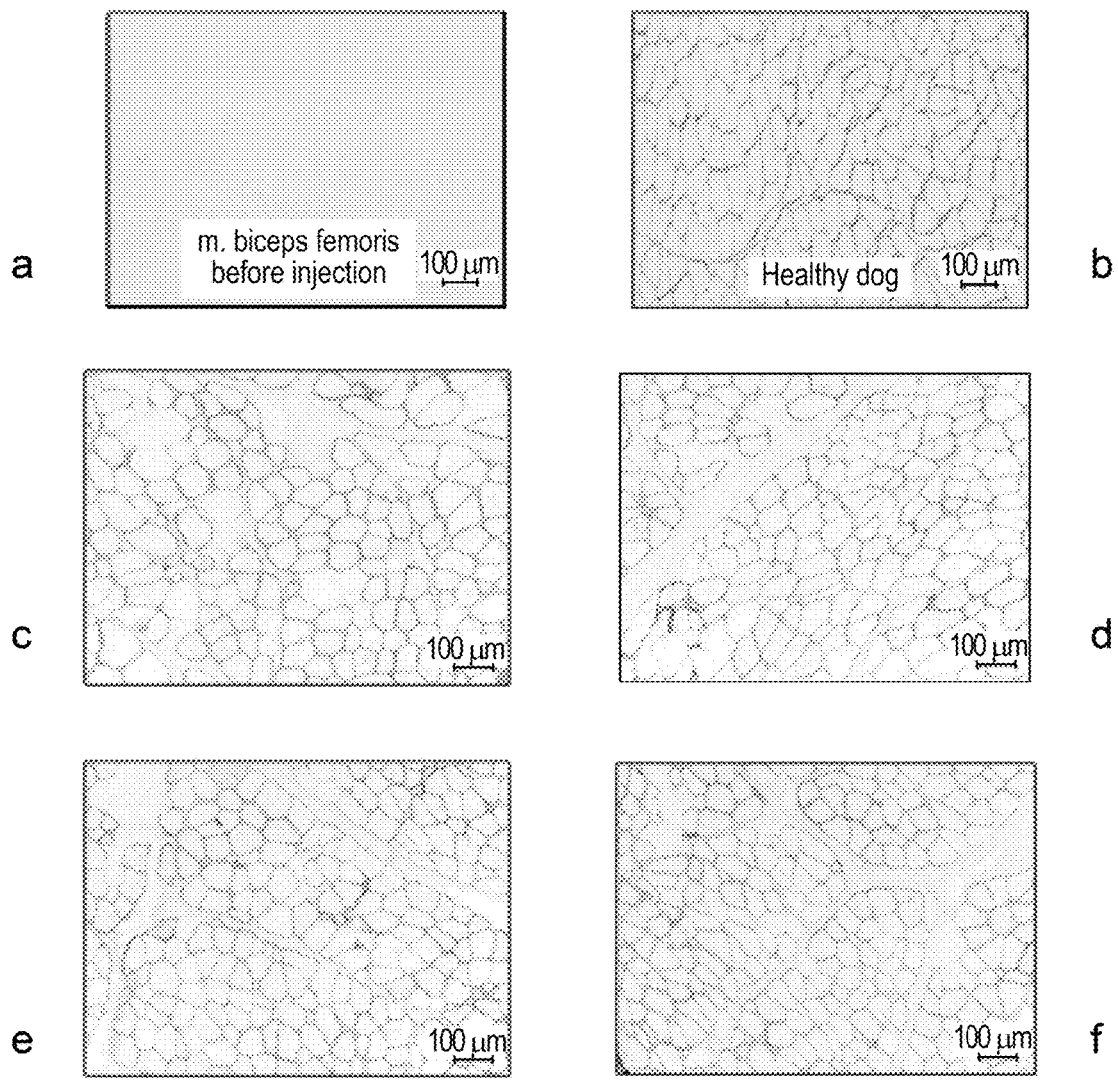
FIG. 3.
Figure 3:
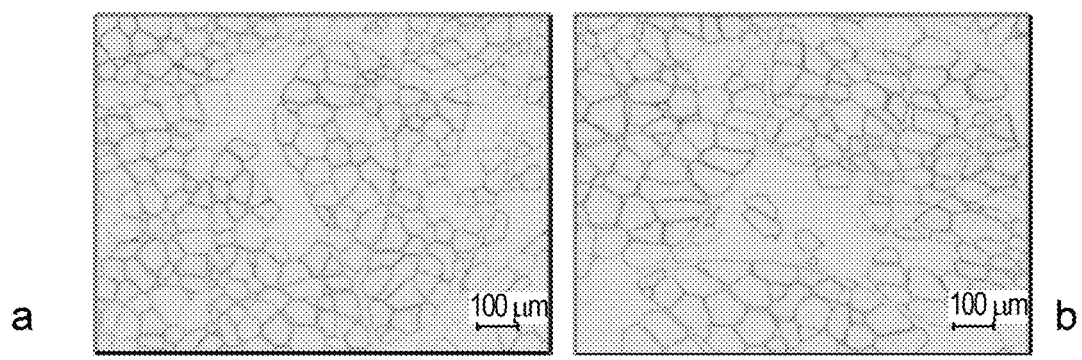

Following the methodology described above, the percentage of muscle fibers expressing the dystrophin polypeptide, 3 months post systemic delivery of the vector, was investigated. The results for GRMD Dog 2 are shown on FIG. 3A.

Along with the percentage of fibers expressing the therapeutic transgene, the number of vector genomes per diploid cell (vg/dg) is indicated after following the methodology also described above. For an average of 2-4 vg/dg, the average percentage of fibers expressing dystrophin ranked from 59 to 82% on the biopsies (FIG. 3A c/ to f/), which was interpreted as very encouraging. One can notice the absence of major cell infiltration and a pretty remarkable preserved tissue architecture.

8 months post systemic delivery of the vector, for 1 vg/dg, the percentage of fibers expressing dystrophin was about 50% on the biopsies (FIG. 3B).

All the date available are compiled in Table 2 below:

| Timing | Muscle | μDys 1 % Dys | μDys 1 vg/dg | μDys 2 % Dys | μDys 2 vg/dg | μDys 3 % Dys | μDys 3 vg/dg | μDys 4 % Dys | μDys 4 vg/dg |
|---|---|---|---|---|---|---|---|---|---|
| Before injection | Biceps femoris | <0.5% | <0.003 | <0.5% | <0.003 | <0.5% | <0.003 | <0.5% | <0.003 |
| 3 months p.i. | Ext. carpi radialis R | 62% | 1.3 | 82% | 2.8 | 43% | 2.2 | 71% | 3.4 |
| | Ext. digit. communis R | 68% | 1.2 | 59% | 4.1 | 31% | 2.0 | 73% | 4.7 |
| | Ext. carpi radialis L | 40% | 1.1 | 62% | 6.2 | 61% | 2.6 | 20% | 1.5 |
| | Ext. digit. communis L | 40% | 0.9 | 66% | 2.6 | 42% | 1.8 | 21% | 1.0 |
| 8 months p.i. | Biceps femoris R | N/A | 0.5 | 58% | 1.0 | 9% | 1.0 | | |
| | Biceps femoris L | N/A | 0.9 | 56% | 0.8 | 38% | 1.3 | | |
| 14 months p.i. | Biceps femoris R | 44% | 1.0 | 44% | Pending | | | | |
| | Biceps femoris L | 36% | 0.7 | 40% | Pending | | | | |

Moreover, a further quantification of the vector genome copies found in the tissues of GRMD dog 3, 7, 5 months post injection, is shown in the table below:

TABLE 3

Vector genome copies found in the muscles of GRMD3 at sacrifice (7.5 months post-injection).

| | Tissu | vg/dg |
|---|---|---|
| Skeletal muscles of the right forelimb | m. flexor carpi ulnaris | 0.16 |
| | m. extensor digitorum communis | 0.25 |
| | m. flexor digitorum superficialis | 0.12 |
| | m. flexor carpi radialis | 0.19 |
| | m. extensor carpi radialis | 0.97 |
| | m. pectoralis | 1.01 |
| | m. deltoideus | 1.86 |
| Skeletal muscles of the left forelimb | m. flexor carpi ulnaris | 0.24 |
| | m. extensor digitorum communis | 0.56 |
| | m. flexor digitorum superficialis | 0.11 |
| | m. flexor carpi radialis | 0.13 |
| | m. extensor carpi radialis | 0.29 |
| | m. pectoralis | 2.47 |
| | m. deltoideus | 1.88 |
| Skeletal muscles of the body | m. paravertebral lumbar | 0.82 |
| | m. intercostales externi | 0.35 |
| | m. rhomboideus cervicis | 1.42 |
| | m. rectus abdominis | 0.68 |
| Skeletal muscles of the right hind limb | m. biceps femoris | 1.03 |
| | m. tibialis cranialis | 1.70 |
| | m. semi-membranous | 2.06 |
| | m. semi-tendinous | 1.33 |
| | m. gluteus superficialis | 0.56 |
| | m. vastus lateralis | 0.46 |
| | m. sartorius | 0.80 |
| | m. gastrocnemius lateralis | 0.81 |
| | m. extensor digitorum longus | 0.53 |
| | m. gracilis | 0.22 |
| Skeletal muscles of the left hind limb | m. biceps femoris | 1.26 |
| | m. tibialis cranialis | 0.96 |
| | m. semi-membranous | 0.39 |
| | m. semi-tendinous | 0.15 |
| | m. gluteus superficialis | 1.11 |
| | m. vastus lateralis | 2.19 |
| | m. sartorius | 0.30 |
| | m. gastrocnemius lateralis | 0.83 |
| | m. extensor digitorum longus | 0.25 |
| | m. gracilis | 0.37 |
| Diaphragm | diaphragm | 1.26 |
| Heart | heart (right + left ventricles) | 1.78 |
| | heart (septum + part of the atrioventricular node) | 0.97 |

In a very interesting manner, it is observed that even at this late time point, a significant amount of transgenic particles is detected in all the skeletal muscles of the body (even at distance of the injection site, i.e. the right cephalic vein), but also in the heart and in the diaphragm. This is in favor of an excellent biodistribution of the transgene within the whole organism.

Figure 4:
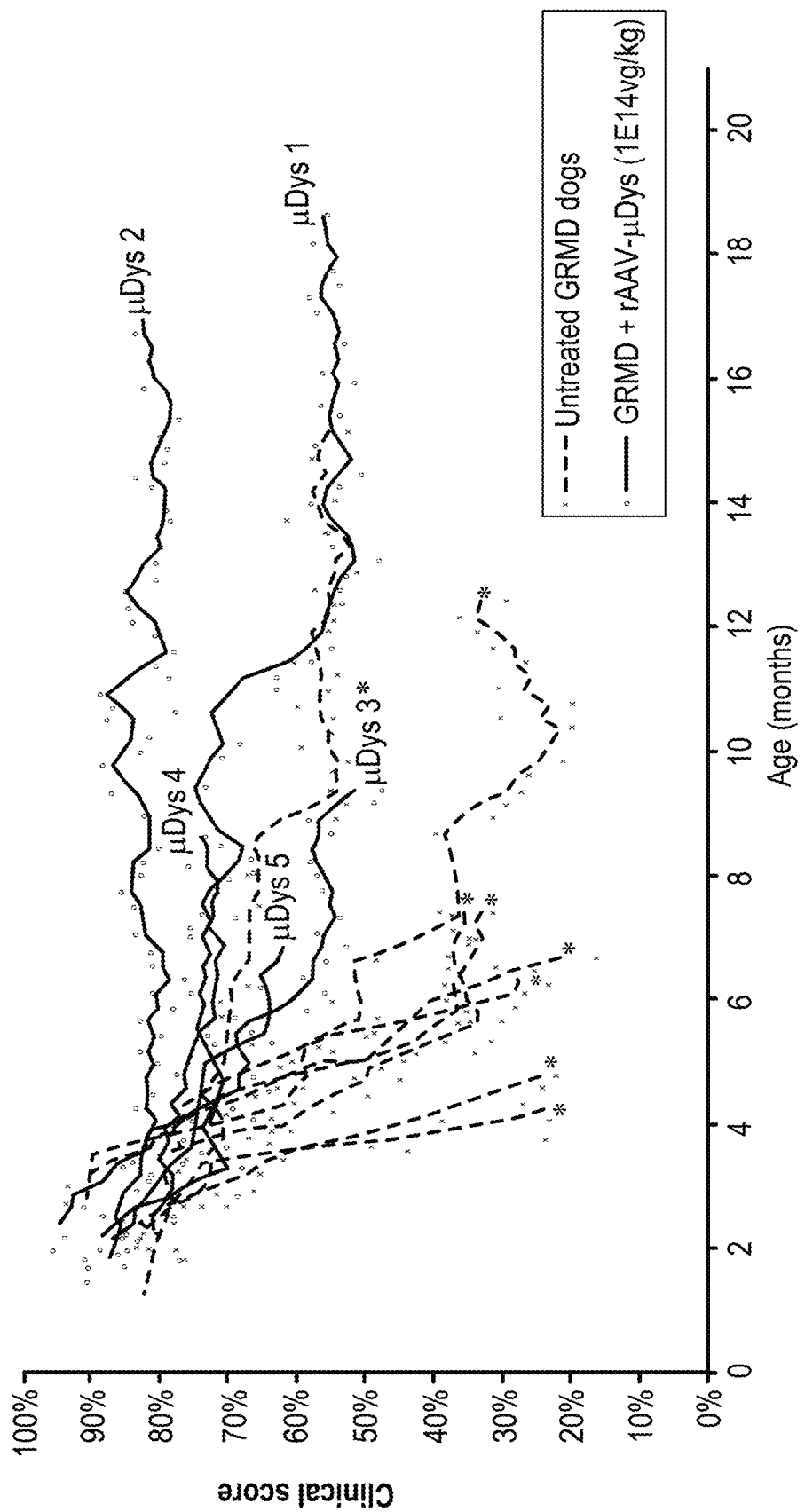
FIG. 4: Data on clinical score obtained in the GRMD cohort that has received $10^{14}$ vg/kg of rAAV2/8-SPc5.12-cMD vector systemic at the age of 2 months. * means that the dog is no longer alive

Clinical evaluation:

Preliminary data on clinical evaluation of the 5 treated GRMD dogs was performed as described above against 8 other untreated age-matched GRMD dogs. FIG. 4 shows, at different post vector injection time points, an improvement of the clinical score based essentially on dysphagia, breathing, ptyalism, global activity. 100% scoring corresponds to healthy individuals. Even if clinical outcomes may vary between treated individuals within the same group (as it is often the case between untreated GRMD), these results suggest that the treated GRMD animals exhibit so far a rather stable phenotype, better than the majority of the untreated animals. The clinical score evaluated in the treated dogs is maintained at a level corresponding to at least 50% of the maximal score obtained in healthy dogs (100%), with some animals being above 70%, whereas the clinical score of the large majority of the untreated animals rapidly dropped under 40% even less (FIG. 4).

These data also support an amelioration of the cardiac and respiratory functions in treated dogs and a prolonged survival in comparison with untreated dogs, together with an improved quality of life.

Figure 5:
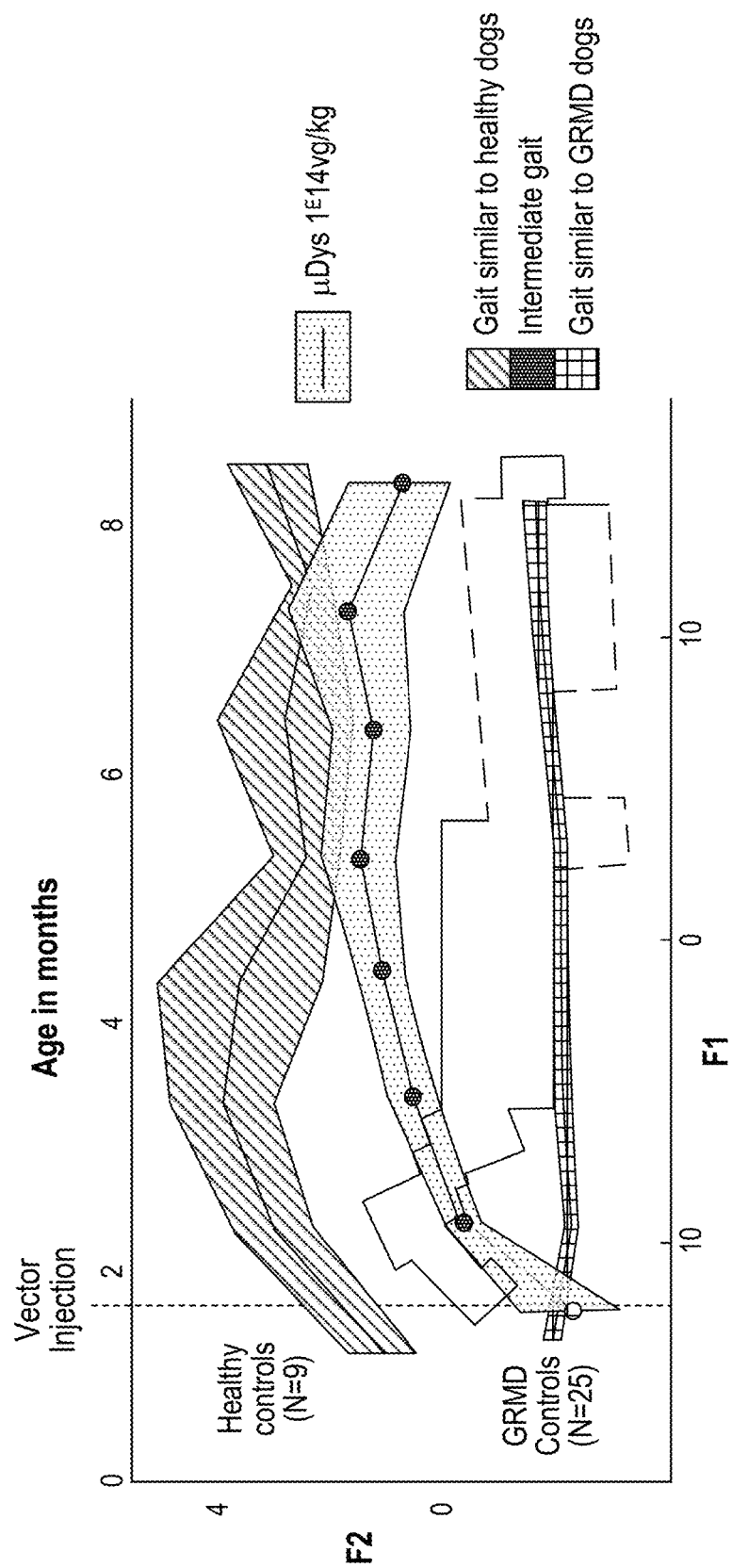
FIG. 5: Data on the Global gait index. Curves were calculated using the model built by Discriminant Analysis and the Data obtained for untreated GRMD and healthy dogs are represented. For the latters, the mean centroid curves and the 95% confidence intervals are shown.

Gait characterization:

As mentioned above, a bi-monthly gait evaluation was performed using the Locometrix® device. Accelerometric was recorded in 3 axes: dorso-ventral (DV), medio-lateral (ML) and cranio-caudal (CC). The gait characterization by a statistical discriminant factor analysis of 7 gait variables (stride frequency, regularity, total power, cranio-caudal power, dorso-ventral power, medio-lateral power and stride length) is shown on FIG. 5.

The results obtained in the injected dogs are positioned relative to the reference data collected during a previous 3D-accelerometers study of disease progression in a group of 25 untreated GRMD and 9 normal dogs (Barthelemy, I., et al., BMC Musculoskelet Disord, 2011. 12: p. 75).

Data show that μdys-treated GRMD dogs developed a global gait index that was very different and much improved to that observed for age-matched untreated GRMD dogs. They rapidly improved their gait performances to exhibited gait very close to that of healthy dogs, after only 3 to 4 months post-injection. From these data, it appears that the μdys-treated GRMD dogs present a gait that is close to healthy dogs of the same breed.

Cardiac and respiratory functions:

The clinical scores shown on FIG. 4 support an amelioration of the cardiac and respiratory function.

Immune response/Toxicity:

The detection of the protein, 3 and 8 months post injection (FIG. 3), as well as the good clinical scores shown on FIG. 4, indicate the absence of adverse and deleterious immune responses to the recombinant AAV vector and to the microdystrophin.

The muscle biopsies (FIG. 3), as well as the good clinical scores shown on FIG. 4, support the absence of toxicity of the gene therapy product.

Figure 6:
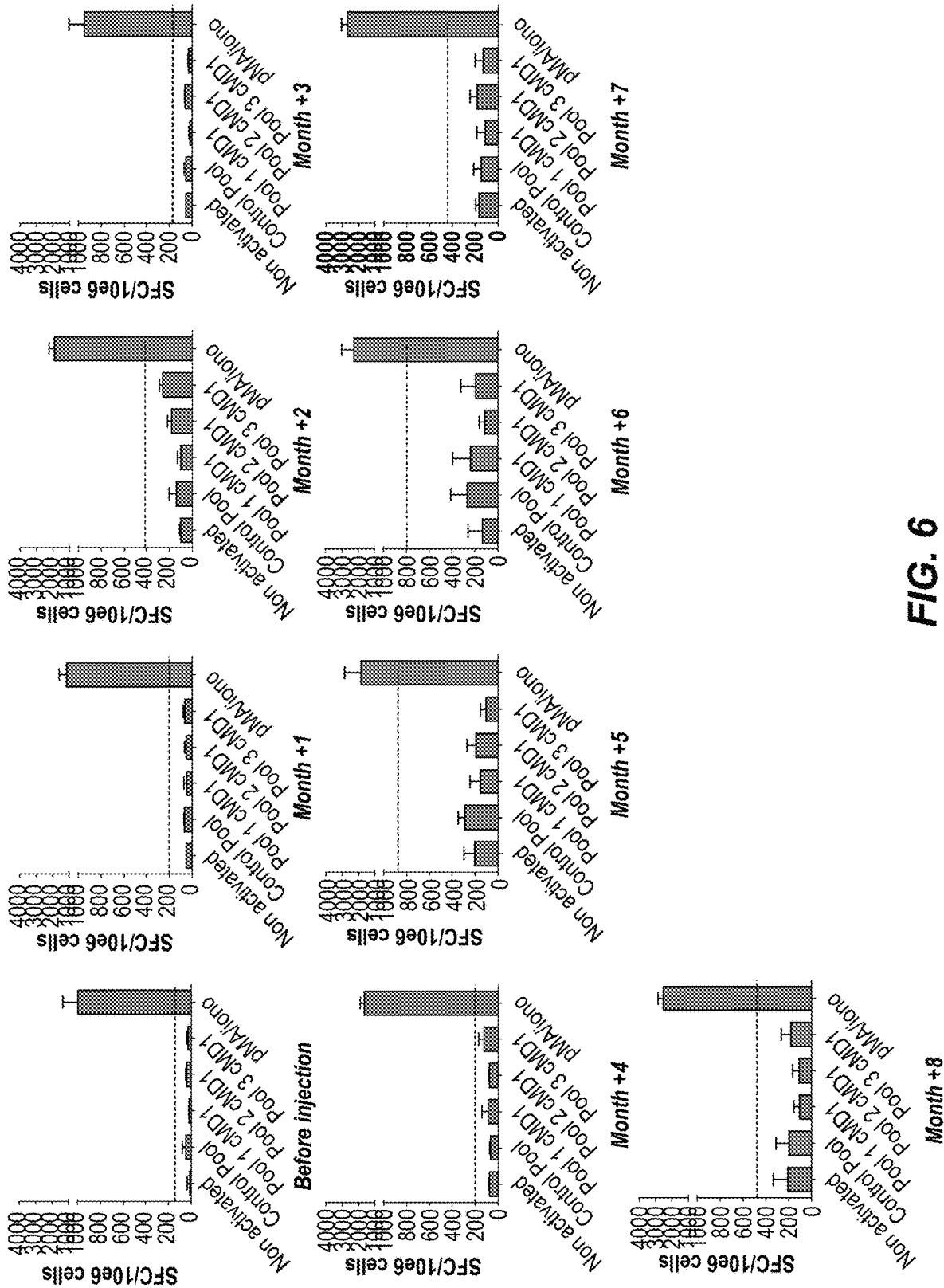
FIG. 6: IFNγ ELISpot using canine μDys peptide pools (kinetics of PBMCs). Data were obtained in the GRMD Dog 2 (ICI) that has received $10^{14}$ vg/kg of rAAV2/8-SPc5.12-cMD vector systemic at the age of 2 months.

In terms of biosafety, the cellular immune response against cMD was evaluated, by interferon gamma Elispot using cMDYF peptides pools incubated on a kinetic of PBMCs (FIG. 6). Whatever the injected dose, none of the injected animals exhibited a detectable secretion of Interferon gamma, suggesting an absence of cellular immune response against cMDYF.

Figure 7:
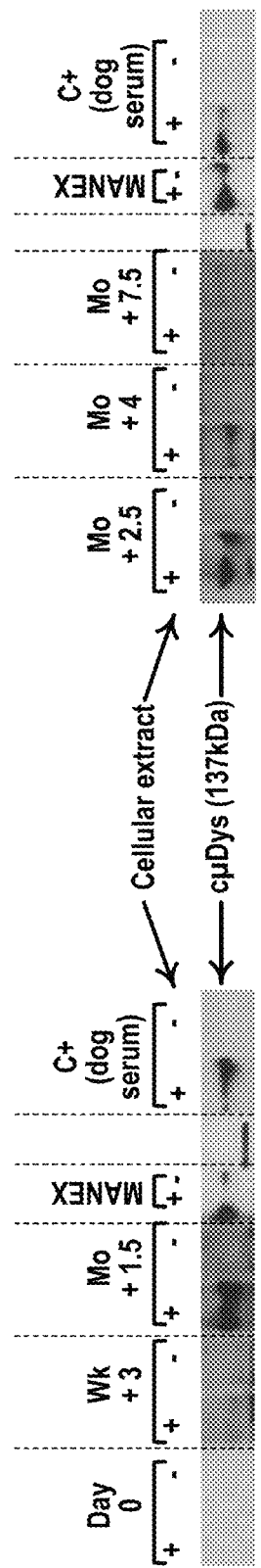
FIG. 7: Detection of anti-dystrophin IgG antibodies by Western-Blot in injected dog sera. Data were obtained in the GRMD Dog 2 (ICI) that has received $10^{14}$ vg/kg of rAAV2/8-SPc5.12-cMD vector systemic at the age of 2 months. The reactivity of each serum was tested on cellular extracts 293 cells transfected (or not) with a pCMV-canine-MD (cμDys). Sera before injection (Day 0) and after injection (week 3, month 1.5, Month 2.5, month 4 and month 7.5) have been tested. Positive controls consisted in the anti-dystrophin antibody MANEX 1011C, and a positive canine serum (C+) from a GRMD dog immunized against dystrophin.

The humoral immune response against cMD was also evaluated by an immuno-western-blot (FIG. 7). All the available results are compiled in Table 4 below:

|  |  | Before injection | Month + 0.5 | Month + 1.5 | Month + 2 | Month + 4 | Month + 7.5 |
| --- | --- | --- | --- | --- | --- | --- | --- |
| $1^E14$ vg/kg | μDys 1 | Nd | Nd | ++ | Nd | Nd | Nd |
|  | μDys 2 | Nd | + | ++ | ++ | + | Nd |
|  | μDys 3 | Nd | Nd | Nd | Nd | Nd | Nd |
|  | μDys 4 | Pending | Pending | Pending | Pending | Pending | Pending |
|  | μDys 5 | Pending | Pending | Pending | Pending | Pending | Pending |

Here, the presence of anti-μdystrophin antibodies was detected in 2 out of 5 dogs injected with $10^{14}$ vg/kg of the AAV-cMD vector. Of importance, this humoral immune response against the cMD is only transient (maximal range of detection=between 2 weeks and 4 months post-injection) and doesn't seem to be associated to any clinical deleterious effect, suggesting that an immune tolerance could occur in these animals.

Survival:

Prolonged survival clearly appears from FIG. 4:

at age 8-9 months, only 2 over 8 untreated GRMD dogs are still alive. On the contrary all the treated GRMD dogs are still alive and healthy;

in a general manner, the life expectancy of untreated GRMD dogs is around 12 months with a very bad clinical state at this age. On the contrary, the 2 treated GRMD dogs tested for long-term follow up (μDys 1 and 2) remain alive after this deadline (with an age of 19 and 17 months, respectively) and are in a good clinical state.

Therapeutic dose:

This study reveals that $10^{14}$ vg/kg, a relatively low dose for systemic administration, is an appropriate dose in terms of efficiency and toxicity in dogs.

CONCLUSIONS:

Altogether, these functional data correlated well with a substantial expression of dystrophin polypeptide (>50% microdystrophin-expressing fibers) on intermediate muscle biopsies. They show the therapeutic effect of the MD microdystrophin construct and support that the systemic delivery may be beneficial to halt/reduce the progression of the disease. The results obtained from this systemic pilot cohort of GRMD indicate that several outcome measures from molecular, pathology and functional aspects support the systemic gene therapy in humans.

This study brings the proof of concept that the SPc5.12-cMD therapeutic cassette encoding for a sequence optimized microdystrophin and encapsidated in the AAV8 capsid provides clinical benefit to the dog model of the Duchenne myopathy after systemic intravenous administration of a single dose. Not only was the microdystrophin polypeptide highly expressed in multiple muscles but it also resulted in gait improvement and improved clinical outcome measures, without adverse immune response. To the knowledge of the inventors, this is the first report of so encouraging and surprising results, especially in the context of a systemic administration.

The invention claimed is:

1. A method of treating Duchenne muscular dystrophy (DMD) in a human, comprising:
systemically administering to a human in need thereof a gene therapy product that comprises an adeno-associated viral (AAV) vector which harbors a nucleic acid sequence encoding a Δ4-R23/ΔCT microdystrophin, wherein the nucleic acid sequence comprises SEQ ID NO: 1, thereby treating DMD in the human.

2. The method according to claim 1, wherein the composition is administered by intravascular injection.

3. The method according to claim 1, wherein the AAV vector is an AAV of serotype 2, 8 or 9.

4. The method according to claim 3, wherein the AAV vector is an AAV8 vector.

5. The method according to claim 1, wherein the composition is administered with a dose less or equal to $10^{15}$ vg/kg.

6. The method according to claim 1, consisting of systemically administering the composition once.

7. The method according to claim 1, wherein the composition is administered by intravenous injection.

8. The method according to claim 3, wherein the AAV vector is an AAV2/8 vector.

9. The method according to claim 5, wherein the composition is administered with a dose between $10^{12}$ vg/kg and $10^{14}$ vg/kg.

* * * * *

UNITED STATES PATENT AND TRADEMARK OFFICE
CERTIFICATE OF CORRECTION

| | | |
|---|---|---|
| PATENT NO. | : 12,023,366 B2 | |
| APPLICATION NO. | : 17/000867 | |
| DATED | : July 2, 2024 | |
| INVENTOR(S) | : George Dickson et al. | |

It is certified that error appears in the above-identified patent and that said Letters Patent is hereby corrected as shown below:

In the Claims

Column 65, Claim 1, Line 28:
"$\Delta 4\text{-}R23/\Delta CT$"
Should read:
--$\Delta R4\text{-}R23/\Delta CT$--.

Signed and Sealed this
Seventeenth Day of September, 2024

*Katherine Kelly Vidal*

Katherine Kelly Vidal
*Director of the United States Patent and Trademark Office*